(12) United States Patent
Chang et al.

(10) Patent No.: US 6,218,155 B1
(45) Date of Patent: Apr. 17, 2001

(54) PLANTS AND PROCESSES FOR OBTAINING THEM

(75) Inventors: Ming-Tang Chang; Peter Lewis Keeling, both of Ames, IA (US)

(73) Assignee: Zeneca Limited, London (GB)

( * ) Notice: Subject to any disclaimer, the term of this patent is extended or adjusted under 35 U.S.C. 154(b) by 0 days.

(21) Appl. No.: 08/987,837

(22) Filed: Dec. 9, 1997

Related U.S. Application Data

(63) Continuation of application No. 08/474,063, filed on Jun. 7, 1995, now abandoned, which is a continuation-in-part of application No. 08/346,602, filed on Nov. 29, 1994, now abandoned, which is a continuation-in-part of application No. 08/263,921, filed on Jun. 21, 1994, now abandoned.

(51) Int. Cl.$^7$ .............................. C08B 21/00; A27L 1/05
(52) U.S. Cl. ...................... 435/101; 536/102; 536/1.11; 800/263; 800/271; 127/29
(58) Field of Search .................................. 800/263, 271; 426/578; 127/29; 536/102, 1.11; 435/101

(56) References Cited

U.S. PATENT DOCUMENTS

| | | |
|---|---|---|
| 4,428,972 | 1/1984 | Wurzburg et al. . |
| 4,767,849 | 8/1988 | Friedman et al. . |
| 4,770,740 * | 9/1988 | Friedman et al. ..................... 127/29 |
| 4,774,328 | 9/1988 | Friedman et al. . |
| 4,789,557 | 12/1988 | Friedman et al. . |
| 4,789,738 | 12/1988 | Friedman et al. . |
| 4,791,997 | 12/1988 | Friedman et al. . |
| 4,792,458 | 12/1988 | Friedman et al. . |
| 4,798,735 * | 1/1989 | Friedman et al. ..................... 426/578 |
| 4,801,470 | 1/1989 | Friedman et al. . |
| 5,004,864 | 4/1991 | Robertson et al. . |
| 5,349,123 | 9/1994 | Shewmaker et al. . |
| 5,516,939 * | 5/1996 | Pearlstein et al. ..................... 426/578 |

FOREIGN PATENT DOCUMENTS

| | | |
|---|---|---|
| 94/22291 | 10/1994 | (WO) . |
| 94/24264 | 10/1994 | (WO) . |

OTHER PUBLICATIONS

Neyra, Carlos A. "Biochemical Basis of Plant breeding" vol. I, Carbon metabolism, Chapter 8, Synthesis, and breakdown of starch. pp. 130–143. CRC Press, 1985.*

Boyer et al. "Interaction of hte amylose extender and waxy mutants of maize." The Journal of Heredity. 67:209–214, 1976.*

Murai et al., Phaseolin Gene from Bean is Expressed After Transfer to Sunflower Via Tumor–Inducing Plasmid Vectors, Science, Nov. 1983, pp. 476–481.

Boyer, "Synthesis and Breakdown of Starch", Biochemical Basis of Plant Breeding, vol. 1, Chapter 8, pp. 133–146.

Napoli, Introduction of a Chimeric Chalcone Synthase Gene into Petunia results in Reversible Co–Suppression of Homologous Genes in trans, The Plant Cell. vol. 2, pp. 279–289.

van der Krol et al., "Inhibition of Flower Pigmentation by Antisense CHS Genes: Promotor and Minimal Sequence Requirements for the Antisense Effect", Plant Molecular Biolog., 14, pp. 457–466, 1990.

van der Krol et al., "Flavonoid Genes in Petunia: Addition of a Limited No. of Gene Copies May Lead to a Suppression of Gene Expression", The Plant Cell, vol. 2, Apr. 1990.

Yamada et al., "A Novel Type of Corn Starch from a Strain of Maize", Starke, 30, (1978), No. 5.S, 145–148.

Sprague (editor): Corn and Corn Improvement, No. 18 in the series Agronomy, 1977.

Yamada, T. et al., "A Novel Type of Corn Starch From a Strain of Maize", Starch, pp. 145–148, vol. 30, (Sep.–Oct., 1974).

Holder, D.G. et al., "Interaction of Shrunken–2 and Sugary–1 in Dosage Series in Corn Endosperm[1]", Crop Science, pp. 647–648, vol. 14. (May 1978).

* cited by examiner

*Primary Examiner*—Gary Benzion
(74) *Attorney, Agent, or Firm*—Nixon & Vanderhye pc

(57) ABSTRACT

The invention relates to a transgenic or mutated plant having genomic material which alters the normal starch synthesis pathway within the plant. More specifically, the present invention relates to a plant having a genotype which creates new forms of starch in significant quantity. Particularly, the invention relates to grain having an embryo with a genotype heterozygous for two or more wild type genes (for example, Aa/Bb) and an endosperm having a genotype heterozygous for such genes (for example, AAa/BBb or AAa/bbB or aaA/BBb or aaA/bbB) and the starch produced therefrom.

38 Claims, 15 Drawing Sheets

PLANTS AND PROCESSES FOR OBTAINING THEM

This is a continuation of application Ser. No. 08/474,063, filed Jun. 7, 1995; now abandoned which is a CIP of 08/346,602 filed Nov. 29, 1994; now abandoned which is a CIP of 08/263,921 filed Jun. 21, 1994 now abandoned.

FIELD OF THE INVENTION

The invention relates to a transgenic or mutated plant having genomic material which alters the normal starch synthesis pathway within the plant. More specifically, the present invention relates to a plant having a genotype which creates new forms of starch in significant quantity. Particularly, the invention relates to grain having an embryo with a genotype heterozygous for two or more wild type genes (for example, Aa/Bb) and an endosperm having a genotype heterozygous for such genes (for example, AAa/BBb or AAa/bbB or aaA/BBb or aaA/bbB) and the starch produced therefrom.

Such grain are produced by pollinating a plant having a genotype homozygous recessive for at least one gene and wild type for another gene (for example, aa/BB) with pollen from another plant having a genotype homozygous recessive for at least one other gene and wild type for the other gene (for example, AA/bb).

BACKGROUND OF THE INVENTION

Most plants produce and store starch. These plants have a starch synthesis pathway for starch production. The amount of starch produced varies with the type of plant. The most commonly known starch producing plants are the cereal grains. These cereals include rice, maize, sorghum, barley, wheat, rye, and oats. Additionally, the potato family, including the sweet potatoes and certain fruits, like the banana, are known as starch producing.

Starch is an important end-product of carbon fixation during photosynthesis in leaves and is an important storage product in seeds and fruits. In economic terms, the starch produced by the edible portions of three grain crops, wheat, rice and maize, provide approximately two-thirds of the world's food calculated as calories.

Starch from plants is used in various ways. For example, it can be extracted and used for cooking and food processing. Starch can be left in the grain or plant and used for animal and human consumption. Starch can also be used in the distillation process for processing alcohols, for example, starch can be converted into ethanol. Additional starch can convert to high-fructose syrup and other industrial components.

Starch is defined in the dictionary as a granular solid which is chemically a complex carbohydrate which is used in adhesives, sizes, foods, cosmetics, medicine, etc. More generally, starch is comprised of amylose and amylopectin. Amylose and amylopectin is synthesized in the plastid compartment (the chloroplast in photosynthetic cells or the amyloplast in non-photosynthetic cells). Different plants generate differing proportions of amylopectin and amylose. Furthermore, the different branching patterns of amylopectin and different chain lengths of amylose and amylopectin chains gives rise to different starch properties. Thus, the fine structure of amylose and amylopectin is different in different plants so that the branching patterns and chain-lengths vary considerably resulting in new and novel properties which are useful in different applications. Until now there have been four ways of making starches with special properties: (i) using starches extracted from different plant species, (ii) using starches extracted from mutant lines of particular plants, (iii) using natural and mutant starches which had been chemically modified, and (iv) using natural and mutant starches which had been physically modified. In all cases the new starches were valuable because of the special properties provided for by the new starch type.

It is known that mutant genes in plants affect the properties of the starch. A variety of starch related mutant genes in maize have been identified and some have been cloned. These mutant genes were named according to the physical appearance (phenotype) of the maize kernel or the properties of the starch. These recessive mutant genes include waxy (wx), sugary (su) [which includes but is not limited to sugary-1 (su1), sugary-2 (su2), sugary-3 (su3), sugary4 (su4)] dull (du), amylose extender (ae), horny (h), shrunken (sh) which includes, but is not limited to, shrunken-1 (sh-1), shrunken-2 (sh-2). Some of these recessive gene mutants produce an isoform of a known enzyme in the starch synthesis pathway. The recessive mutant alleles of these genes result in a complete or nearly complete reduction in the activity of a specific isoform of one enzyme (hereinafter defined as complete reduction of enzyme isoform activity) in the pathway when homozygous in a plant or when expressed in sufficient levels in a transgenic plant. This change in the starch synthesis pathway causes the formation of starches with different properties.

Several crop varieties are known which produce different types of starch. The type of quality of starch makes it suitable for certain purposes, including particular methods of processing or particular end-uses. Naturally-occurring maize mutants produce starches of differing fine structure suitable for use in various food products and other applications. Although known mutants produce altered starch, some of these lines are not suitable for crop breeding and/or for the farmers' purposes. For example, they can give relatively poor yields, and/or are difficult to process and/or can have poor germination.

In order to generate different starches, single and double mutant plants have been bred. A single mutant is a plant that is homozygous for one recessive mutant gene. For example, waxy maize, waxy rice, waxy barley, and waxy sorghum have the homozygous mutant waxy (wx) gene. Whilst starches from waxy genotypes have very little or no amylose, another mutation known as amylose extender (ae) results in starch with high amylose. A double mutant is a single plant that has homozygous (or full expression) of two recessive mutant genes. For example, the wxfl1 double mutant is taught in U.S. Pat. 4,789,738. Many other novel starches have been provided in other starch patents in which double or triple mutants are generated (for example, U.S. patent Ser. Nos.: 4,789,557, 4,790,997, 4,774,328, 4,770,710, 4,798,735, 4,767,849, 4,801,470, 4,789,738, 4,792,458 and 5,009,911 which describe naturally-occurring maize mutants producing starches of differing fine structure suitable for use in various food products). The present invention is highly surprising in light of these applications because it produces altered starch and does not require double or triple mutants.

Normal starch is defined as starch which is not chemically modified (by people) or which is produced from a plant that has the expected genes (wild type) regulating the starch synthesis pathway. For ease of reading, double lower-case letters, for example aa, shall refer to a homozygous recessive mutant gene, double upper-case letters, for example AA, shall refer to a homozygous non-mutant gene (wild type), and one upper-case and one lower-case letter, for example Aa, shall refer to a non-homozygous set of genes, one mutant, one non-mutant. Different letters in the same size shall mean different genes; "aa/bb") would be a double mutant; "aa/bB") would be a single homozygous mutant gene and a heterozygous mutant gene in the genome of the plant. For purposes of this application, the order of any three letters on one side of the slash can be interchanged and will not define the parent that donated the gene. For example, AAa/bbB is defined to be equivalent to aAA/bBb, AaA/Bbb, AaA/bBb, aAA/Bbb, and the like.

Although maize plants and the embryo are diploid, maize endosperm is triploid. The endosperm genotype has two gene doses which are inherited from the female plant portion and one gene dose which is inherited from the pollen or male plant portion. Thus, if a single mutant plant "aa" is used as the female and crossed to a non-mutant plant "AA" male, then the endosperm in the kernel of this female plant would be "aaA". If a non-mutant plant "AA" is crossed to a mutant plant "aa" with the non-mutant as the female, the endosperm on the kernel of the female plant will be "Aaa", because two gene doses come from the female and one from the male plant. Classic teaching is that the mutant gene is recessive and the non-mutant is dominant; therefore, the starch produced by a plant having the following gene doses in the endosperm "aaA" or "AAA" or "AAa" results in the normal starch in the expected amounts. However, the endosperm of a homozygous mutant plant "aa" acting as the female crossed to a homozygous mutant plant "aa" acting as the male plant results in the endosperm having the gene dosage "aaa". This endosperm gives starch with different properties from normal starch. Likewise, the starch from a double mutant having of an endosperm which is "aaa/bbb" shows differences in starch properties from normal starch. These starch differences are useful in that they can replace chemically modified starches or be used with or in foodstuffs or as grain in alcohol production or in general starch industrial applications.

Clearly, it appears that production of grain having starch with different physical properties of starch requires the crossing of two mutated plants to generate grain which is homozygous recessive for both genes. Mutant plants are less predictable than standard plants.

There is a recurrent problem with the production of grain and extraction of starch from double mutant hybrids and/or inbreds and some single mutants. The. amount of starch produced is usually less than the amount of starch produced by the non-mutant plant, there is also a loss in starch granule size and/or starch granule integrity. This problem with known double mutant lines which produce structurally-altered-starch in which the quantity of starch produced in the crop is relatively low can result in poor germinability of the seed. Furthermore, the reduced starch yield of the seed appears to be unavoidable since the mutations cause the normal starch synthesis functioning of the cells to be disrupted. There remains a need for a way to produce grain having structurally altered starch structurally altered starch or altered properties without a significant loss of yield or reduced starch granule size or integrity.

SUMMARY OF THE INVENTION

A first object of the present invention is to provide a method of developing hybrid plants having altered complex carbohydrate content of the grain which does not require the crossing of double mutant inbreds.

An object of the present invention is to provide plants that produce grain having altered starch properties.

Another object of the present invention is to provide transgenic plants that produce grain having altered starch properties.

Yet another object of the present invention is to provide a maize plant that produces both altered starch and larger quantities of starch than the associated mutant plants produce.

Still another object of the present invention is to provide new plants which contain genes which produce incomplete reduction of the activity of at least two isoforms of the specific enzymes in the starch synthesis pathway of the plant.

A further object of the present invention is to provide maize plants which have endosperms with the genotype "AAa/BBb or AAa/bbB or aaA/BBb or aaA/bbB".

Yet another object of the present invention is a plant producing the following endosperm genotype "wxwxWX/AeAeae".

Still an additional object of the present invention is to provide the altered starch which can be produced by plants having the genotype "AAa/BBb or AAa/bbB or aaA/BBb or aaA/bbB".

The present invention broadly covers a method of producing intermutants generally which have the endosperm genotype of AAa/bbB and certain intermutants including endosperm which is waxy, waxy, amylose extender (wxwxWx/AEAEae). The method of producing grain with altered starch qualities includes the steps of planting the female acting parent which is capable of flowering. The female parent having substantially complete reduction of at least one specific isoform enzyme in the starch synthesis pathway. This can be by a homozygous recessive mutant or by the partial down regulation of the wild type gene through the use of a cloned gene using techniques generally known as antisense or co-suppression or sense-down regulation. Additionally the female has incomplete reduction of at least one specific isoform enzyme in starch synthesis pathway. This can be by a heterozygous recessive mutant gene or partial down regulation. Regardless of how the female is produced it should only act as the female portion. To assure this a step includes eliminating the first parent's capability to produce pollen. The method includes the step of pollinating the female acting parent with the pollen of the male acting parent which is a non-mutant parent. Harvesting the grain produced by said first parent. Additionally, the method can include the extraction of starch from the grain.

This invention also encompasses a plant having genomic material which includes genes which give incomplete reduction of the activity of at least two specific isoforms of the enzymes in the starch synthesis pathway of said plant. And the starch it produces which has altered structure when compared with the starch formed by a similar plant as described but which comprises genomic material which does not form isoforms of the enzymes in the starch synthesis pathway of the plant.

A plant which forms said starch in grain such as cereal grains. Grain produced by a female plant having for example a waxy genotype (wxwx) crossed with a male plant having for example an amylose extender genotype (aeae) in which the genotype of the endosperm of the grain is wxwxWx/AeAeae.

In other words, the present invention is a starch producing plant comprising genomic material which includes genes which give incomplete reduction of the activity of at least two specific isoforms enzymes in the starch synthesis pathway of said plant whereby said plant produces substantially more starch than said plant would produce if said genes gave complete reduction of the activity of the same two specific isoforms of the enzymes within the starch synthesis pathway.

Grain having an endosperm that has two genes which contain one gene dose of recessive mutant gene and two doses of wild type; and, having two gene doses of recessive mutant and one dose of wild type. Within this description the invention encompasses grain having endosperm genotypes of wxwxWx/AeAeae, or aeaeAe/WxWxwx, or wxwxWx/DuDudu, or duduDu/WxWxwx, or aeaeAe/DuDudu, or duduDu/AeAeae, or wxwxWx/SuSusu, or susuSu/WxWxwx, or aeaeAe/SuSusu, or susuSu/AeAeae, or duduDu/SuSusu, or susuSu/DuDudu and the like.

The starch from a grain having a genotype of wxwxWx/AeAeae. The starch from a grain having a genotype of Aeaeae/WxWxwx.

A female plant having a diploid genotype of aa/BB and having a triploid genotype of aaA/BBb where a is a recessive mutant gene and A is the wild type gene, and b is a recessive mutant gene and B is the wild type gene such that the starch is altered from the normal starch where a and b can be selected from ae, wx, sh, bt, h, su, fl, op and B and A can be selected from Ae, Wx, Sh, Bt, H, Su, Fl, Op.

BRIEF DESCRIPTION OF THE DRAWINGS

The present invention will now be described, by way of illustration, by the following description and examples with reference to the accompanying drawings of which.

DETAILED DESCRIPTION OF THE INVENTION

Figure 1:
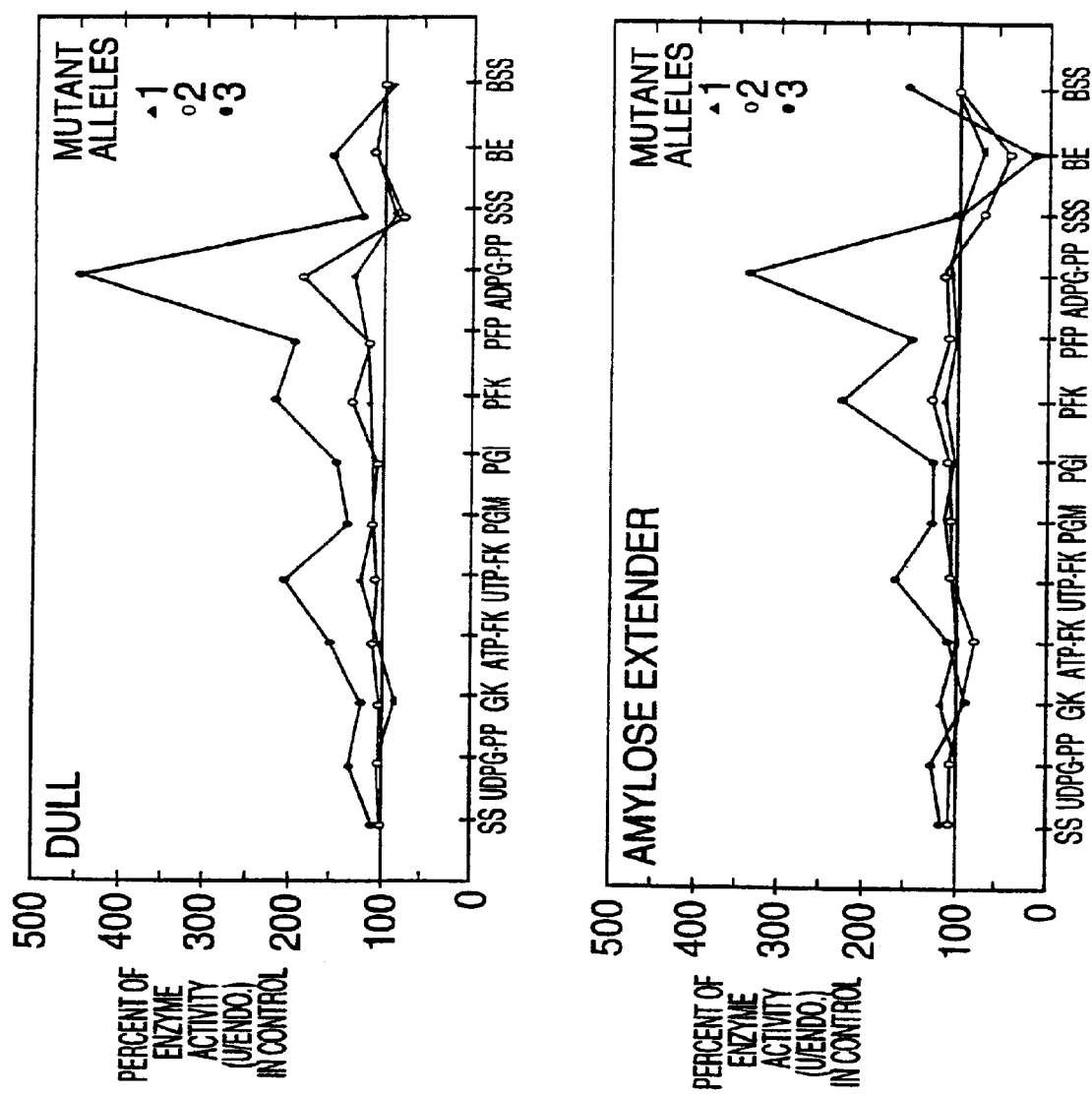
FIG. 1 is a graph of enzyme activity for different gene doseages of a single mutant.

Broadly then the present invention is an improved crop line which has manipulated expression of at least two starch-synthesizing enzymes which alter the amount and type of starch, and, consequently, alters the grain produced by the plant.

It has been discovered that plants which contain at least two genes which partially down regulated or reduce the activity of specific isoforms of enzymes in the starch synthesis pathway will surprisingly produce significant amounts of starch in the grain and will produce altered starch types.

Specialty maize or mutant plants differ from "normal" maize because of its altered endosperm. The changed endosperm gives rise to a high degree of starch branching, or changed sugar content, or different kernel structure. The endosperm of course is formed by the sperm and ovule, and the selection of both parents effects the endosperm's makeup.

The present invention can be formed by two principle methods. The invention can be formed within a selected crop species by the use of mutant breeding. And the invention can be formed in various plants by the use of transformation of the plants with genes which partially down regulate two or more enzymes in the starch synthesis pathway. More particularly, down regulation of one of the isoforms of the enzyme in the starch synthesis pathway to approximately ⅓ of the normal activity and ⅔ of the normal activity in the other isoform enzyme or down regulation of both isoform enzymes in the starch synthesis pathway approximately ⅔ of the normal activity. Each of these methods has its own advantages.

First, the use of mutants to develop unique grain and starches in cereal crops is widely known. However, the present invention is highly unique and surprising because it was expected to produce grain having normal starch characteristics. The following table explains how unexpected the present invention is.

TABLE 1

| Genotype of Parents (female 1st) | Genotype of endosperm | Type of Starch | Starch Yield |
|---|---|---|---|
| Wild-Type | AA*AA | AAA | Normal | Normal |
| Gene dosage | AA*aa | AAa | Normal | Normal |
| | aa*AA | aaA | Normal | Normal |
| Single mutant | aa*aa | aaa | Altered | Lowered |
| Double mutant | aa/bb*aa/bb | aaa/bbb | Altered | Lowered |
| PRESENT INVENTION - EXPECTED RESULTS | | | | |
| Intermutant | aa/BB*AA/bb | aaA/BBb | Normal | Normal |
| | AA/BB*aa/bb | AAa/BBb | Normal | Normal |
| | aa/bb*AA/BB | aaA/bbB | Normal | Normal |
| | aa/bb*aa/BB | aaa/bbB | Normal | Normal |
| | aa/BB*aa/bb | aaa/BBb | Normal | Normal |
| PRESENT INVENTION - ACTUAL RESULTS | | | | |
| Intermutant | aa/BB*AA/bb | aaA/BBb | Altered | Medium to |
| | AA/BB*aa/bb | AAa/BBb | Altered | high~70% |
| | aa/bb*AA/BB | aaA/bbB | Altered | of normal |
| | aa/bb*aa/BB | aaa/bbB | Altered | |
| | aa/BB*aa/bb | aaa/BBb | Altered | | aa = mutant gene (homozygous)
AA = wild type (or non-mutant homozygous gene)
* = signifies a cross-pollination between two varieties
aa/bb = two mutant genes (both homozygous)

Clearly, since the genotype of the endosperm of the present invention shown in the table did not have completely recessive genes, the starch yield and structure was expected to be normal. In fact, according to the present invention, the grain does not evidence normal starch structure altered starch. Historically, when altered starch is produced only small quantities are usually produced. The altered starch of the present invention was surprisingly produced in larger than expected quantities. Additionally, production of this starch is much simpler than the production of double mutant crops. Previously only single mutant hybrids have been used extensively for large-scale starch production. Previously, to develop the double mutants, both parents had to carry both mutations which requires significant research and development efforts and results in poor starch yield and poor seed germinability. Heretofore, only small-scale production of the double mutants has been possible.

The present invention encompasses a method of producing grain with altered starch qualities which includes the steps of planting a parent which is capable of flowering, this parent having substantially complete reduction of at least one specific isoform of an enzyme (A) in the starch synthesis pathway and having no reduction of at least one other specific isoform of an enzyme (B) in the starch synthesis pathway. The other parent has no reduction of one isoform of an enzyme (A) and substantially complete reduction of at least one other specific isoform of an enzyme (B) in the starch synthesis pathway. It is then necessary to eliminate said first parents capability to produce pollen and allow pollination to proceed from said second mutant parent, and finally harvesting the grain produced by said first parent. Additionally, the method can include the extraction of starch from the grain and using said starch as a specialty starch for a variety of uses for which it is shown to be valuable.

The following examples of the present invention are given for illustrative purposes only. These examples are not intended to limit the type or the uses of the present invention. The present invention or the grain or starch or sugar thereof can be useful in, but may not be limited to, the preparation of foodstuff, paper, plastics, adhesives, paints, production of ethanol and corn syrup products.

EXAMPLE 1

The physical properties of various embodiments of the present invention (similar genotypes are from different maize crosses). These tables display data well known to people skilled in the arts of evaluating new and novel starches. Data on moistures, and percent oil, protein, solubles and starch are useful in evaluating yield and milling potential. Starch DSC (Differential Scanning Calorimetry) data are valuable for evaluating starch cooking and gelatinization properties. Starch particle size data are valuable for making decisions on starch milling and separation properties. Brabender and starch paste data are most important for evaluating a new starch's potential for improved food applications where particular starch thickening and pasting and gelatinization properties are mostly desired. Such data when interpreted as a whole collection of information enable one skilled in the art to decide whether to conduct further more detailed tests of the starches properties and potential.

| Genotype | % Moisture | % Starch | % Protein | % Oil | % Solubles |
|---|---|---|---|---|---|
| aeae/wx | 8.01 | 72.12 | 11.30 | 3.63 | 6.51 |
| aeae/wx | 8.00 | 71.34 | 11.74 | 3.79 | 6.41 |
| aeae/wx | 8.03 | 67.52 | 12.61 | 3.67 | 7.01 |
| aeae/ae | 8.13 | 60.11 | 14.59 | 6.60 | 10.14 |
| su1su1/wx | 8.18 | 69.66 | 12.09 | 4.03 | 6.91 |
| dudu/wx | 7.98 | 71.10 | 11.57 | 3.92 | 6.61 |
| dudu/su1 | 7.90 | 70.53 | 11.67 | 3.93 | 6.81 |
| flfl/o | 7.78 | 70.23 | 11.60 | 4.23 | 6.59 |
| su1su1/du | 7.81 | 69.00 | 12.20 | 4.77 | 7.98 |
| su1su1/ae | 7.88 | 69.03 | 12.27 | 4.88 | 8.02 |
| su1su1/su2 | 7.95 | 69.67 | 12.28 | 4.55 | 7.49 |

TABLE 2

| | | | - Corn Data | | | | |
|---|---|---|---|---|---|---|---|
| Entry | Background | S93 Row | % Moisture | % Starch | % Protein | % Oil | % Solubles |
| 1 | aeaewx | 4660 | 9.15 | 64.80 | 14.58 | 4.47 | 7.64 |
| 2 | aeaesu | 4636 | 9.27 | 66.25 | 14.77 | 4.54 | 7.40 |
| 3 | aeaedu | 4612 | 9.24 | 66.01 | 14.65 | 4.73 | 7.80 |
| 4 | wxwxae | 4600 | 9.07 | 65.72 | 13.91 | 4.38 | 8.14 |
| 5 | wxwxsu | 4648 | 9.06 | 66.03 | 14.79 | 4.08 | 7.83 |
| 6 | wxwxdu | 4624 | 8.77 | 65.32 | 15.62 | 4.27 | 8.23 |
| 7 | susuae | 4594 | 8.85 | 64.83 | 13.11 | 4.71 | 8.49 |
| 8 | susudu | 4672 | 8.73 | 65.39 | 13.20 | 5.01 | 8.35 |
| 9 | susudu | 4618 | 8.77 | 65.15 | 14.52 | 4.35 | 8.26 |
| 10 | single ae | 4582 | 9.14 | 60.52 | 15.19 | 5.95 | 9.29 |
| 11 | single wx | 4654 | 8.83 | 65.44 | 14.04 | 4.77 | 9.43 |
| 12 | single su | 4630 | 7.75 | 54.98 | 14.25 | 6.50 | 9.78 |
| 13 | duduae | 4588 | 8.97 | 69.26 | 12.30 | 4.89 | 6.85 |
| 14 | duduwx | 4666 | 8.88 | 70.43 | 11.25 | 4.40 | 6.96 |
| 15 | dudusu | 4642 | 9.48 | 70.43 | 13.48 | 4.67 | 6.92 |
| 16 | single du | 4606 | 8.50 | 65.54 | 12.02 | 6.03 | 9.33 |

TABLE 2-continued

Starch Data

| Entry | Background | S93 Row | % Moisture | % Starch | % Protein | % Oil | % Amylose | L-max |
|---|---|---|---|---|---|---|---|---|
| 1 | aeaewx | 4660 | 3.82 | 86.44 | 1.68 | 0.18 | 31.60 | 597.1 |
| 2 | aeaesu | 4636 | 6.51 | 86.95 | 1.56 | 0.20 | 31.74 | 603.9 |
| 3 | aeaedu | 4612 | 5.22 | 86.44 | 1.70 | 0.11 | 33.38 | 598.8 |
| 4 | wxwxae | 4600 | 7.33 | 87.89 | 0.39 | 0.09 | 21.10 | 601.1 |
| 5 | wxwxsu | 4648 | 7.27 | 85.87 | 1.32 | 0.09 | 24.68 | 591.7 |
| 6 | wxwxdu | 4624 | 7.31 | 86.07 | 1.12 | 0.10 | 24.57 | 595.2 |
| 7 | susuae | 4594 | 8.19 | 86.32 | 0.93 | 0.07 | 29.00 | 604.5 |
| 8 | susudu | 4672 | 8.09 | 87.16 | 0.52 | 0.08 | 27.86 | 599.6 |
| 9 | susudu | 4618 | 7.67 | 84.20 | 0.60 | 0.12 | 30.82 | 601.1 |
| 10 | single ae | 4582 | 7.16 | 83.31 | 1.37 | 0.15 | 65.55 | 602.1 |
| 11 | single wx | 4654 | 8.30 | 85.16 | 0.51 | 0.14 | 0.43 | xx |
| 12 | single su | 4630 | 6.82 | 80.92 | 5.08 | xx | 29.32 | 598.4 |
| 13 | duduae | 4588 | 6.58 | 84.31 | 0.62 | 0.17 | 29.86 | xx |
| 14 | duduwx | 4666 | 11.08 | 84.77 | 0.48 | 0.16 | 28.74 | xx |
| 15 | dudusu | 4642 | 8.48 | 87.34 | 0.62 | 0.16 | 26.07 | XX |
| 16 | single du | 4606 | 8.36 | 80.70 | 0.46 | 0.08 | 37.88 | 608.9 |

(Starch Data)

| Entry | Genotype | % Moisture | % Starch | % Protein | % Oil | % Amylose | L-max |
|---|---|---|---|---|---|---|---|
| 1 | ae ae/wx | 9.56 | 83.84 | 0.63 | 0.05 | 29.44 | 593.1 |
| 2 | ae ae/wx | 7.96 | 85.94 | 0.70 | 0.05 | 27.89 | 596.6 |
| 3 | ae ae/wx | 11.71 | 82.54 | 0.82 | 0.05 | 42.54 | 595.1 |
| 4 | ae ae/ae | 6.09 | 84.17 | 1.24 | 0.14 | 63.60 | 602.4 |
| 5 | su1 su1/wx | 4.37 | 90.00 | 0.56 | 0.09 | 28.36 | 600.0 |
| 6 | du du/wx | 5.95 | 88.50 | 0.61 | 0.09 | 27.98 | 596.9 |
| 7 | du du/su1 | 6.93 | 82.66 | 0.69 | 0.10 | 29.98 | 600.8 |
| 8 | fl fl/o | 9.24 | 82.72 | 0.93 | 0.14 | 29.29 | 596.8 |
| 9 | su1 su1/du | 9.01 | 84.82 | 0.71 | 0.02 | 29.57 | 600.8 |
| 10 | su1 su1/ae | 7.78 | 84.81 | 0.63 | 0.03 | 29.90 | 600.8 |
| 11 | su1 su1/su2 | 7.61 | 85.02 | 0.49 | 0.02 | 29.68 | 602.3 |
| 12 | White waxy | 18.34 | 94.94db | 0.77 | 0.09 | 2.74 | 526.9 |

Starch DSC Data

| Entry | Genotype | Peak ° C. | Delta H J/g | Peak II ° C. | Onset ° C. | Endset ° C. |
|---|---|---|---|---|---|---|
| 1 | ae ae/wx | 67.7 | 11.67 | 100.0 | 62.6 | 76.6 |
| 2 | ae ae/wx | 66.5 | 10.33 | 96.8 | 61.9 | 74.8 |
| 3 | ae ae/wx | 74.6 | 10.00 | 100.8 | 68.8 | 83.4 |
| 4 | ae ae/ae | 81.0 | 11.83 | xx | 66.0 | 107.4 |
| 5 | su1 su1/wx | 69.7 | 12.00 | 98.3 | 64.2 | 77.7 |
| 6 | du du/wx | 72.2 | 11.50 | 99.5 | 66.6 | 82.3 |
| 7 | du du/su1 | 70.2 | 9.67 | 98.4 | 65.7 | 78.3 |
| 8 | fl fl/o | 71.4 | 12.33 | 100.9 | 67.1 | 80.7 |
| 9 | su1 su1/du | 68.8 | 7.83 | 99.5 | 63.2 | 79.1 |
| 10 | su1 su1/ae | 68.1 | 10.33 | 99.8 | 61.9 | 78.3 |
| 11 | su1 su1/su2 | 67.4 | 12.00 | 96.1 | 61.3 | 79.5 |
| 12 | White waxy | 72.7 | 15.33 | xx | 66.1 | 82.6 |

Starch DSC Data

| Entry | Background | S93 Row | Peak ° C. | Delta H J/g | Peak II ° C. | Onset ° C. | Endset ° C. |
|---|---|---|---|---|---|---|---|
| 1 | aeaewx | 4660 | 73.8 | 11.17 | 99.4 | 67.7 | 82.8 |
| 2 | aeaesu | 4636 | 73.0 | 11.50 | 101.0 | 66.6 | 83.4 |
| 3 | aeaedu | 4612 | 73.3 | 10.83 | 98.6 | 66.7 | 83.0 |
| 4 | wxwxae | 4600 | 72.39 | 12.83 | 99.9 | 67.4 | 81.7 |
| 5 | wxwxsu | 4648 | 73.7 | 12.17 | 98.2 | 68.2 | 81.6 |
| 6 | wxwxdu | 4624 | 73.6 | 11.33 | 99.6 | 69.3 | 80.5 |
| 7 | susuae | 4594 | 72.0 | 10.33 | 97.7 | 67.2 | 79.7 |
| 8 | susudu | 4672 | 71.9 | 9.83 | 98.9 | 67.0 | 79.1 |
| 9 | susudu | 4618 | 72.5 | 10.33 | 97.0 | 68.4 | 79.8 |
| 10 | single ae | 4582 | 84.6 | 15.67 | xx | 68.7 | 106.9 |
| 11 | Single wx | 4654 | 72.5 | 16.17 | xx | 68.1 | 81.4 |
| 12 | single su | 4630 | 70.9 | 5.50 | 100.8 | 63.6 | 77.2 |
| 13 | duduae | 4588 | 71.8 | 13.50 | 100.5 | 67.1 | 81.1 |
| 14 | duduwx | 4666 | 71.9 | 10.17 | 98.8 | 67.2 | 79.5 |
| 15 | dudusu | 4642 | 71.7 | 10.17 | 97.2 | 66.8 | 79.0 |
| 16 | single du | 4606 | 71.6 | 9.50 | 100.1 | 65.8 | 79.8 |

TABLE 2-continued

- Brabender Data

| Entry | Background | S93 Row | Brabender | IR °C. | HP BU | HF BU | CP BU | CF BU |
|---|---|---|---|---|---|---|---|---|
| 1 | aeaewx | 4660 | 460 g/5.5% | 65.0 | 315 | 285 | 940 | 940 |
| 2 | aeaesu | 4636 | 460 g/5.5% | 81.5 | 225 | 225 | 470 | 430 |
| 3 | aeaedu | 4612 | 460 g/5.5% | 84.5 | 180 | 180 | 410 | 380 |
| 4 | wxwxae | 4600 | 460 g/5.5% | 74.0 | 360 | 355 | 590 | 460 |
| 5 | wxwxsu | 4648 | 460 g/5.5% | 74.0 | 325 | 325 | 540 | 470 |
| 6 | wxwxdu | 4624 | 460 g/5.5% | 80.0 | 315 | 270 | 480 | 425 |
| 7 | susuae | 4594 | 460 g/5.5% | 77.0 | 270 | 270 | 610 | 585 |
| 8 | susudu | 4672 | 460 g/5.5% | 77.0 | 295 | 295 | 785 | 610 |
| 9 | susudu | 4618 | 460 g/5.5% | 77.0 | 295 | 295 | 620 | 620 |
| 10 | single ae | 4582 | 460 g/12% | 90.5 | 170 | 170 | 240 | 240 |
| 11 | single wx | 4654 | 460 g/5.5% | 68.0 | 750 | 360 | 415 | 405 |
| 12 | single su | 4630 | 90 g/5.5% | 93.5 | 35 | 35 | 40 | 40 |
| 13 | duduae | 4588 | 460 g/5.5% | 83.0 | 225 | 225 | 545 | 520 |
| 14 | duduwx | 4666 | 460 g/5.5% | 86.0 | 245 | 245 | 600 | 550 |
| 15 | dudusu | 4642 | 460 g/5.5% | 84.5 | 270 | 270 | 620 | 585 |
| 16 | single du | 4606 | 460 g/5.5% | 89.0 | 70 | 70 | 160 | 160 |

IR = initial rise
CP = cooling peak
CF = cooling final

- Brabender Data

| Entry | Genotype | Brabender | IR °C. | HP BU | HF BU | CP BU | CF BU |
|---|---|---|---|---|---|---|---|
| 1 | ae ae/wx | 460 g/5.5% | 83.0 | 220 | 220 | 520 | 460 |
| 2 | ae ae/wx | 460 g/5.5% | 89.0 | 220 | 220 | 540 | 510 |
| 3 | ae ae/wx | 460 g/5.5% | 84.5 | 270 | 270 | 510 | 450 |
| 4 | ae ae/ae | 460 g/12% | 90.5 | 490 | 490 | 1220 | 845 |
| 5 | su1 su1/wx | 460 g/5.5% | 80.0 | 250 | 240 | 595 | 535 |
| 6 | du du/wx | 460 g/5.5% | 83.0 | 280 | 250 | 560 | 470 |
| 7 | du du/su1 | 460 g/5.5% | 50.0/83.0 | 230 | 230 | 575 | 535 |
| 8 | fl fl/o | 460 g/5.5% | 81.5 | 280 | 255 | 630 | 560 |
| 9 | su1 su1/du | 460 g/5.5% | 84.5 | 200 | 200 | 500 | 460 |
| 10 | su1 su1/ae | 460 g/5.5% | 86.0 | 205 | 205 | 455 | 415 |
| 11 | su1 su1/su2 | 460 g/5.5% | 84.5 | 180 | 180 | 420 | 385 |
| 12 | White waxy | 460 g/5.5% | 68.0 | 830 | 220 | 310 | 270 |

- Starch Particle Size Data

| Entry | Background | S93 Row | (Volume Distribution) | | | % Starch Recovery |
|---|---|---|---|---|---|---|
| | | | Mode µm | Mean µm | Median µm | |
| 1 | aeaewx | 4660 | 16.90 | 12.57 | 16.04 | 45.9 |
| 2 | aeaesu | 4636 | 16.63 | 11.82 | 15.23 | 57.9 |
| 3 | aeaedu | 4612 | 16.36 | 11.48 | 15.20 | 52.4 |
| 4 | wxwxae | 4600 | 17.43 | 11.62 | 16.53 | 41.5 |
| 5 | wxwxsu | 4648 | 17.72 | 12.43 | 16.59 | 58.8 |
| 6 | wxwxdu | 4624 | 17.48 | 12.22 | 16.26 | 54.1 |
| 7 | susuae | 4594 | 16.36 | 11.96 | 15.66 | 55.5 |
| 8 | susudu | 4672 | 16.65 | 9.83 | 15.29 | 58.7 |
| 9 | susudu | 4618 | 16.36 | 11.82 | 15.61 | 55.9 |
| 10 | single ae | 4582 | 13.09 | 9.07 | 12.25 | 64.0 |
| 11 | single wx | 4654 | 18.03 | 11.99 | 16.85 | 55.7 |
| 12 | single su | 4630 | 7.43 | 5.16 | 7.95 | 5.6 |
| 13 | duduae | 4588 | 16.90 | 11.01 | 15.37 | 50.9 |
| 14 | duduwx | 4666 | 17.19 | 11.85 | 16.21 | 52.5 |
| 15 | dudusu | 4642 | 17.17 | 12.22 | 16.01 | 44.9 |
| 16 | single du | 4606 | 14.41 | 9.77 | 13.19 | 58.9 |

- Starch Particle Size Data

| Entry | Genotype | (Volume Distribution) | | | % Starch Recovery |
|---|---|---|---|---|---|
| | | Mode µm | Mean µm | Median µm | |
| 1 | ae ae/wx | 16.63 | 10.90 | 15.70 | 51.4 |
| 2 | ae ae/wx | 16.12 | 10.44 | 14.92 | 52.8 |
| 3 | ae ae/wx | 15.60 | 10.55 | 14.60 | 59.4 |
| 4 | ae ae/ae | 11.53 | 8.40 | 11.30 | 63.7 |
| 5 | su1 su1/wx | 14.88 | 10.24 | 14.21 | 52.5 |
| 6 | du du/wx | 16.38 | 10.73 | 15.12 | 52.0 |
| 7 | du du/su1 | 15.87 | 11.03 | 14.98 | 53.2 |

TABLE 2-continued

| | | | | | |
|---|---|---|---|---|---|
| 8 | fl fl/o | 16.12 | 10.73 | 15.35 | 69.3 |
| 9 | su1 su1/du | 15.87 | 10.73 | 14.92 | 53.7 |
| 10 | su1 su1/ae | 15.11 | 7.85 | 14.35 | 48.5 |
| 11 | su1 su1/su2 | 15.85 | 10.33 | 14.20 | 58.4 |
| 12 | White waxy | 17.19 | 8.45 | 14.81 | 71.5 |

-Starch Paste Data

| Entry | Genotype | Brookfield Viscosity CPS, 20 rpm | Gel-24 hr (grams) | Freeze Thaw Cycles |
|---|---|---|---|---|
| 1 | ae ae/wx | 6,200 | 166.6 | 0 |
| 2 | ae ae/wx | 6,700 | 227.2 | 0 |
| 3 | ae ae/wx | 8,000 | 256.3 | 0 |
| 4 | ae ae/ae | 14,250 | 111.1 | 0 |
| 5 | su1 su1/wx | 6,800 | 173.4 | 0 |
| 6 | du du/wx | 6,000 | 141.4 | 0 |
| 7 | du du/su1 | 7,100 | 215.4 | 0 |
| 8 | fl fl/o | 7,500 | 209.4 | 0 |
| 9 | su1 su1/du | 6,300 | 219.7 | 0 |
| 10 | su1 su1/ae | 6,000 | 172.2 | 0 |
| 11 | su1 su1/su2 | 5,500 | 158.8 | 0 |
| 12 | White waxy | 1,900 | 15.3 | 3 |

- Starch Paste Data

| Entry | Background | S93 Row | Brookfield Viscosity CPS, 20 rpm | Gel-24 hr | Freeze Thaw Cycles |
|---|---|---|---|---|---|
| 1 | aeaewx | 4660 | 25,000 | 151.8 | 0 |
| 2 | aeaesu | 4636 | 6,500 | 240.1 | 0 |
| 3 | aeaedu | 4612 | 3,150 | 216.6 | 0 |
| 4 | wxwxae | 4600 | 5,600 | 159.5 | 0 |
| 5 | wxwxsu | 4648 | 6,100 | 126.4 | 0 |
| 6 | wxwxdu | 4624 | 5,700 | 114.4 | 0 |
| 7 | susuae | 4594 | 8,700 | 254.8 | 0 |
| 8 | susudu | 4672 | 12,000 | 272.8 | 0 |
| 9 | susudu | 4618 | 10,250 | 233.6 | 0 |
| 10 | single ae | 4582 | 2,500 | 53.7* | 0 |
| 11 | single wx | 4654 | 3,100 | 13.3 | 3 |
| 12 | single su | 4630 | 275 | 29.0 | 0 |
| 13 | duduae | 4588 | 7,200 | 226.5 | 0 |
| 14 | duduwx | 4666 | 7,300 | 233.4 | 0 |
| 15 | dudusu | 4642 | 5,100 | 332.9 | 0 |
| 16 | single du | 4606 | 1,650 | 99.3 | 0 |

*came out as a plug

DEFINITIONS

DIFFERENTIAL SCANNING CALORIMETRY (DSC)

IR denotes initial rise

HP denotes heat peak

HF denotes heat final

CP denotes cooling peak

CF denotes cooling final.

BROOKFIELD VISCOMETER

The Brookfield Viscometer measures shear-strength (in centipoise, cP) and stability of starch pastes.

BRABENDER VISCO-AMYLOGRAPH DATA

Pasting temperature denotes the temperature of paste formation.

Peak Viscosity denotes the temperature needed to provide a useable paste.

Viscosity at 95C denotes the ease of cooking of the starch.

Viscosity at 50C denotes the setback in paste viscosity during cooling of a hot paste.

Viscosity after 1 hour at 50C denotes the stability of the cooked paste.

CORN PERCENT PROTEIN, STARCH, OIL AND MOISTURE

Percentages of oil starch and protein in corn give a measure of starch yield how recoverable the starch is.

STARCH PERCENT PROTEIN, STARCH, OIL AND MOISTURE

Percentages of oil starch and protein in starch give a measure of how well purified the starch is and indicates millability.

PERCENT AMYLOSE AND L-MAX

These data provide a measure of apparent amylose levels in starch.

STARCH PARTICLE SIZE DATA

Starch particle size gives an indication of starch yield and recoverability through the milling process.

SHORT HAND aeaewx in table 2 refers to aeaeAE/wxWxWx, likewise duduwx=duduDU/wxWxWx Thorough out this table the wild type is not listed.

FIG. 1 is a graph of enzyme activities for individual gene-doseages (e.g., MMM, mMM, mmM, mmm) of mutant alleles of the single mutants of amylose extender and dull. These data show the enzyme activities of sucrose synthase (SS), UDP-glucose pyrophosphorylase (UDPG-PP), glucokinase (GK), fructokinase (FK), phosphoglucomutase (PGM), phosphoglucose isomerase (PGI), ATP-dependent phosphofructokinase (PFK), PPi dependent phosphofructokinase (PFP), ADP-glucose pyrophosphorylase (ADPG-PP), soluble starch synthase (SSS), branching enzyme (BE) and bound starch synthase (BSS). Enzyme activities are presented as percentages relative to the wild-type control (MMM). In the case of the full mutants (mmm) there is a dramatic effect on expression levels of various enzymes in the pathway of starch synthesis. In the case of the partial mutants (mMM and mmM) there is almost no detectable change in expression levels. These data indicated that the alteration in starch quality observed with the single mutants is a consequence of the overexpression of several enzymes as well as elimination of the enzyme coded for by the mutated allele. By combining two mutant doses (e.g., wxwxWx) with other doses of another mutation (e.g., AeAeae) there would be partial reduction in two enzymes without the overexpression seen in the rest of the pathway.

FIG. 2 is a graph of the DSC scan of starches extracted from grain taken from waxy, amylose extender and common (wild type) corn. Such DSC scans enable one skilled in the art to provide numerical data (see tables in text for data on Peak Temperature, Delta H, Peak II Temperature, Onset Temperature and Endset Temperature). It is particularly noteworthy that the profile of the high amylose starch is different from the common starch and waxy starch.

Figure 2A:
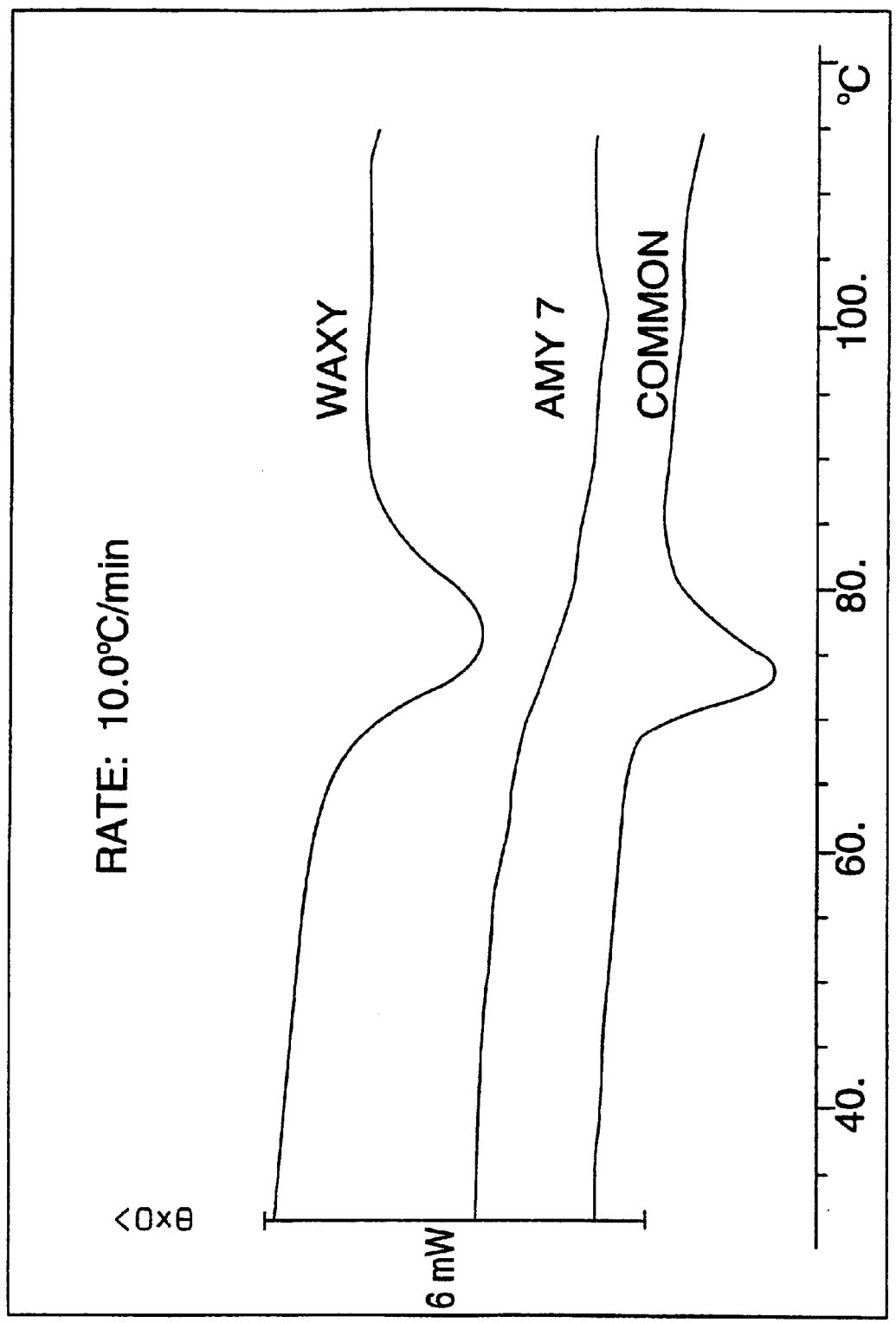
FIG. 2a is a graph of the DSC scan of waxy, amylose extender and common maize.
Figure 2B:
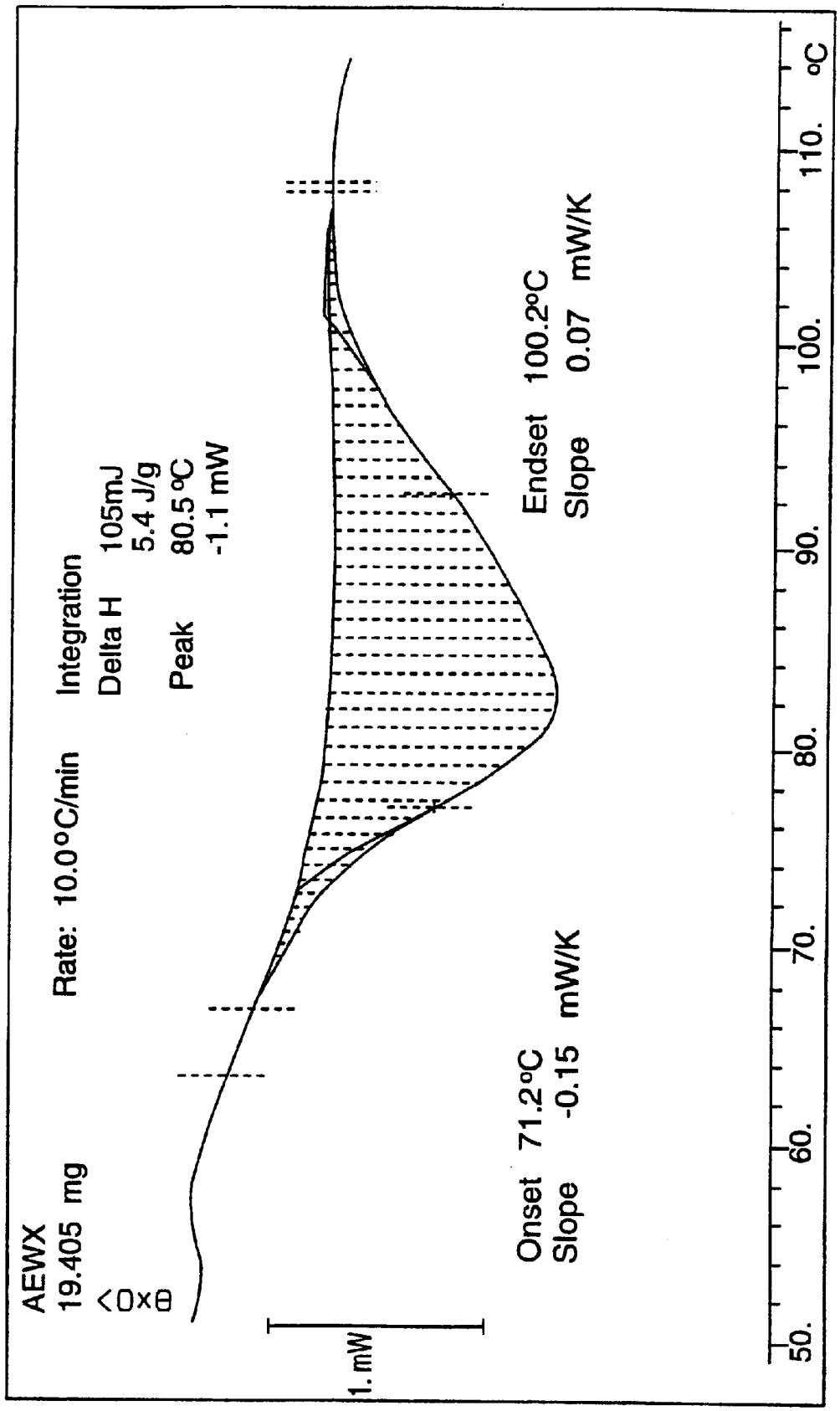
FIG. 2b is a graph of the DSC scan of a double mutant (aeaeae/wxwxwx)

FIG. 2b is a graph of the DSC scan of starches extracted from grain taken from the double mutant (aeaeae/wxwxwx) corn. Such DSC scans enable one skilled in the art to provide numerical data (see tables in text for data on Peak Temperature, Delta H, Peak II Temperature, Onset Temperature and Endset Temperature). It is particularly noteworthy that the profile of the double mutants is different from the data provided in FIG. 2a on common starch and the single mutants, waxy and high amylose.

Figure 2C:
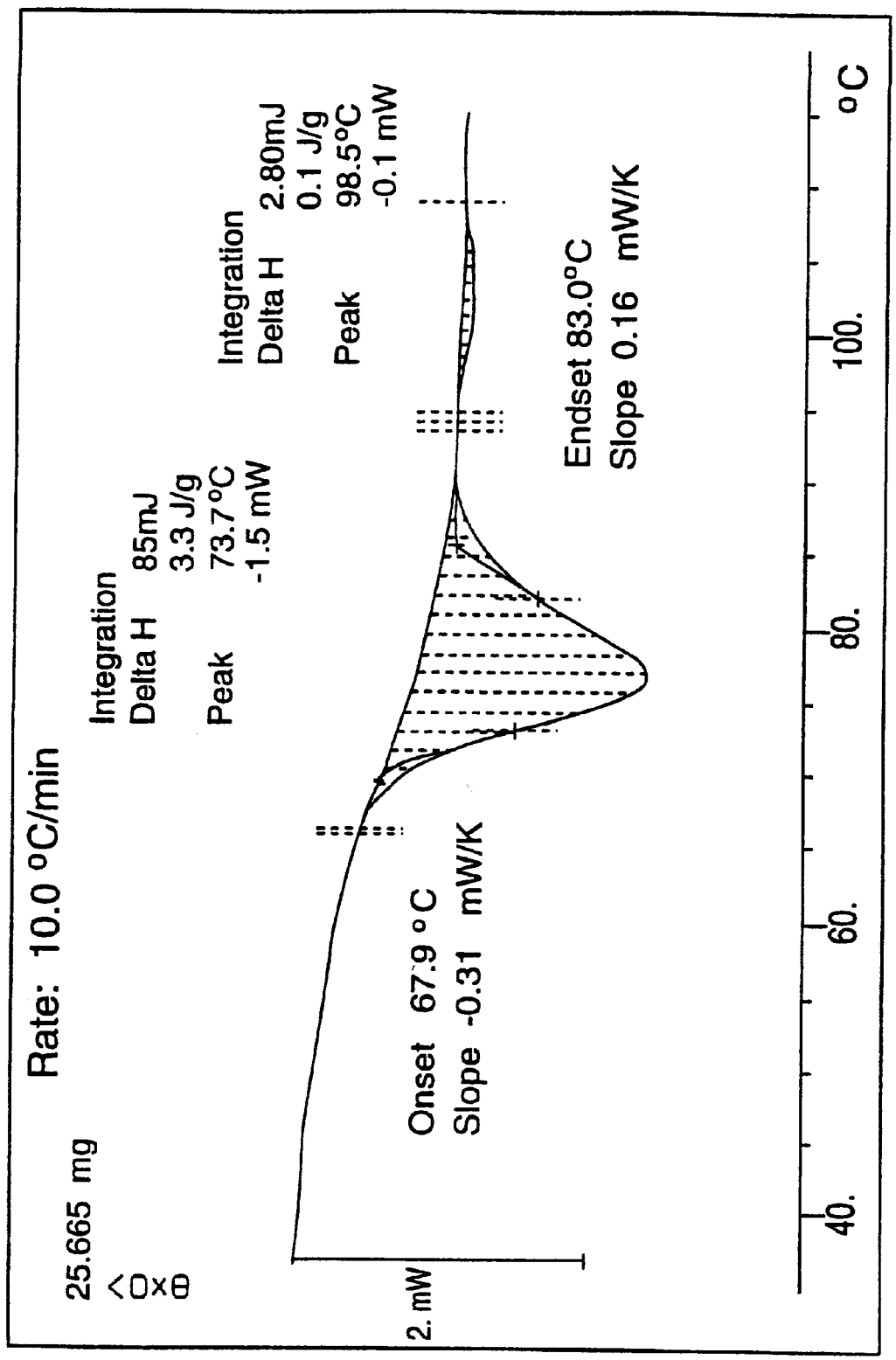
FIG. 2c is a graph of the DSC scan of starch from an intermutant (aeaeAe/wxwxwx).

FIG. 2c is a graph of the DSC scan of starches extracted from grain taken from intermutant (aeaeAe/WxWxwx) corn. Such DSC scans enable one skilled in the art to provide numerical data (see tables in text for data on Peak Temperature, Delta H, Peak II Temperature, Onset Temperature and Endset Temperature). It is particularly noteworthy that the profile of the intermutant starch is different from the starch of the double mutant and appears to be similar to that of waxy starch.

Figure 2D:
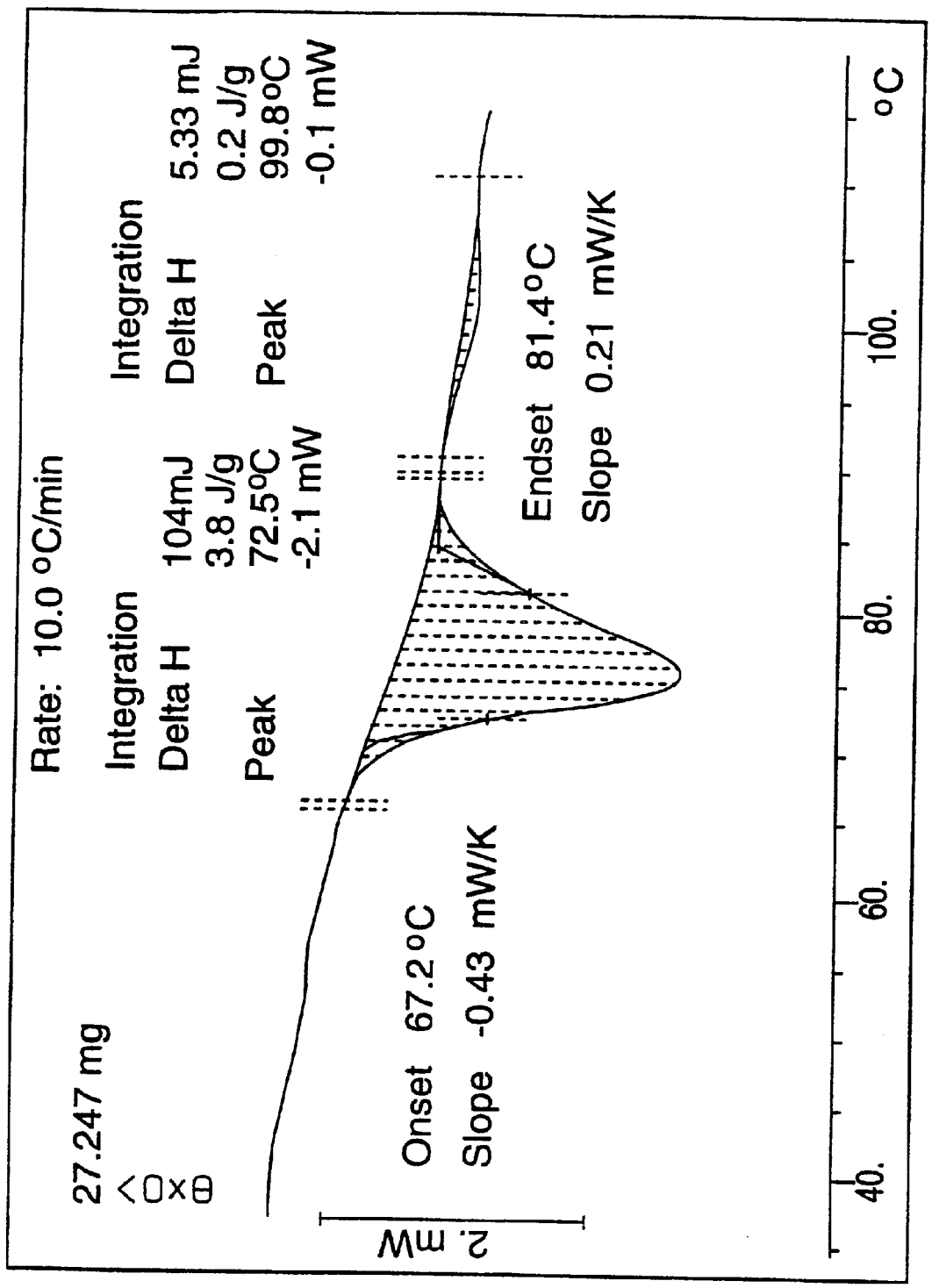
FIG. 2d is a graph of the DSC scan of starch from another intermutant (wxwxWx/AeAeae).

FIG. 2d is a graph of the DSC scan of starches extracted from grain taken from intermutant (wxwxWx/AeAeae) corn. Such DSC scans enable one skilled in the art to provide numerical data (see tables in text for data on Peak Temperature, Delta H, Peak II Temperature, Onset Temperature and Endset Temperature). It is particularly noteworthy that the profile of the intermutant starch is different from the starch of the double mutant and appears to be similar to that of waxy starch.

Figure 3A:
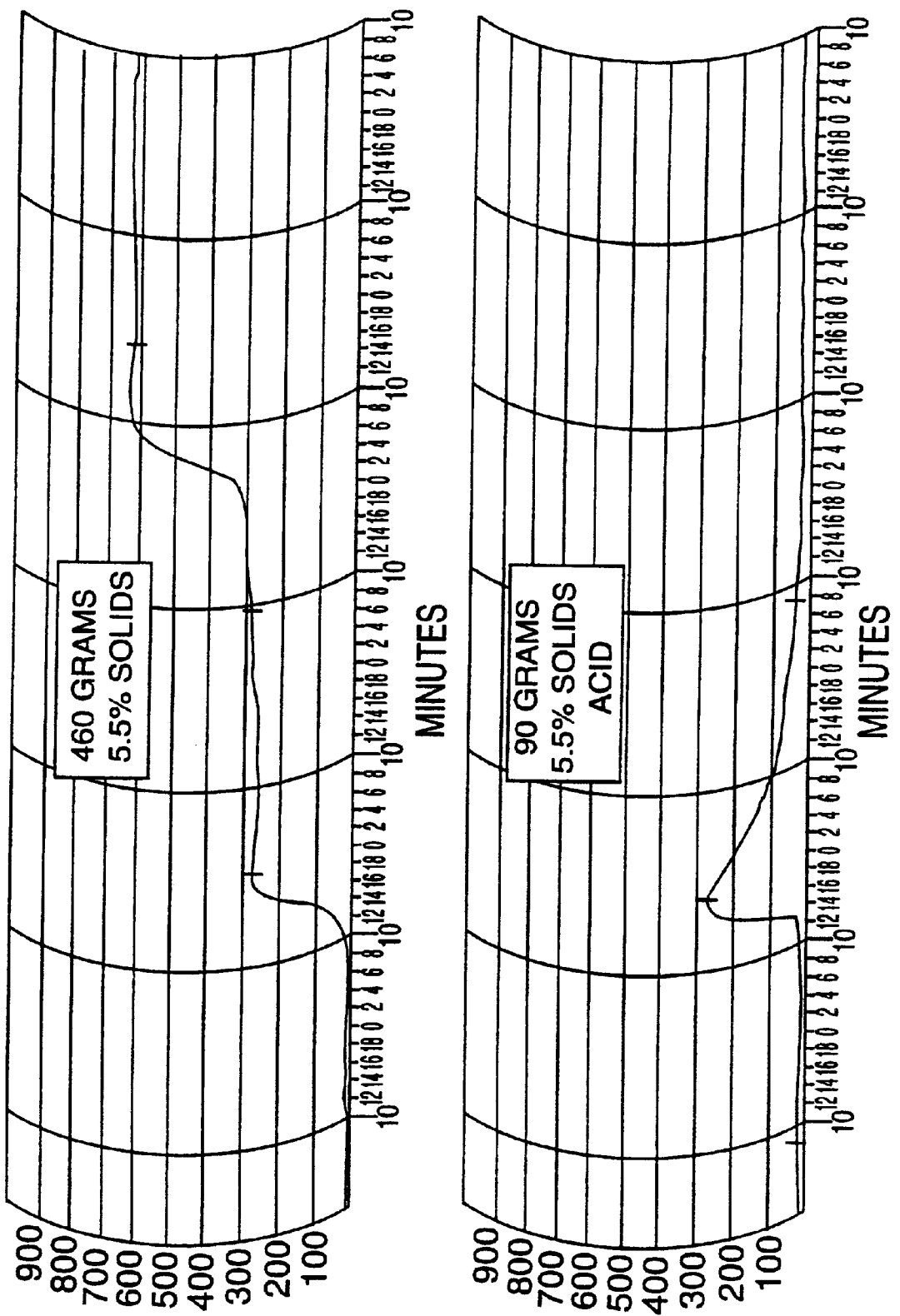
FIG. 3a is a graph of Brabender data of common starch in various pH.

FIG. 3a is a graph of Brabender data taken from common starch in either neutral or acid conditions. Common corn starch shows substantial breakdown in viscosity using acid conditions.

Figure 3B:
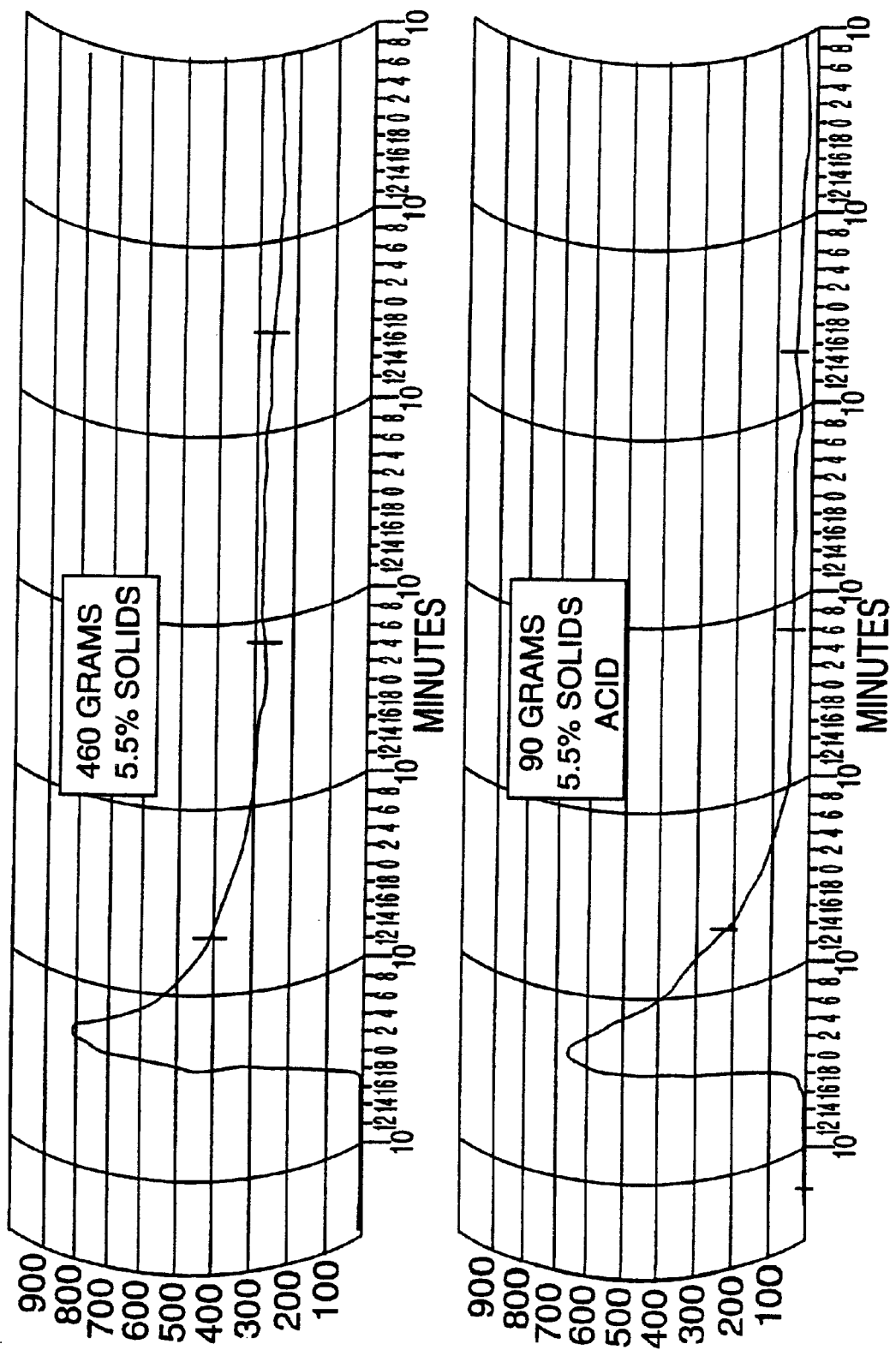
FIG. 3b is a graph of Brabender data of waxy starch in various pH.

FIG. 3b is a graph of Brabender data taken from waxy starch in either neutral or acid conditions. The waxy mutation most particularly affects viscosity of the starch in neutral conditions.

Figure 3C:
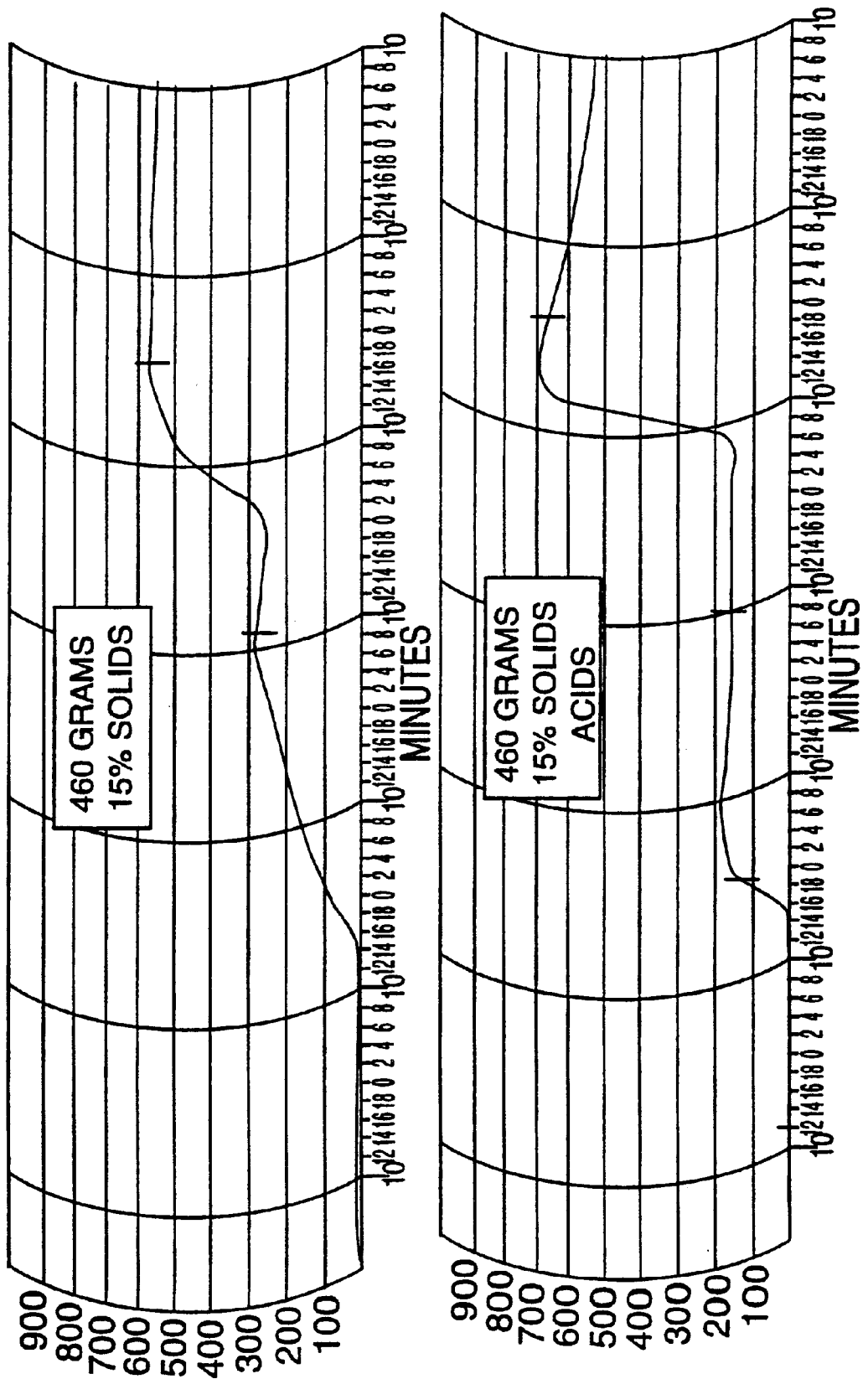
FIG. 3c is a graph of Brabender data of 70% amylose starch in various pH.

FIG. 3c is a graph of Brabender data taken from amylose extender (70% amylose) starch in either neutral or acid conditions. High amylose starches increase in viscosity in either acid or neutral conditions.

Figure 3D:
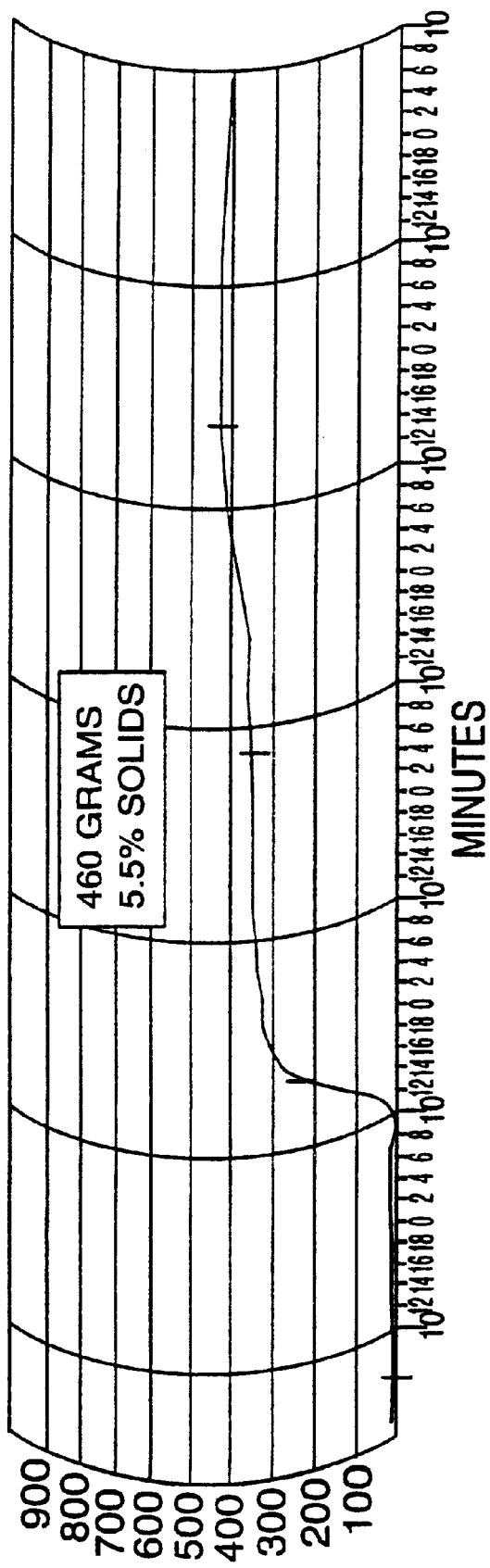
FIG. 3d is a graph of Brabender data of double mutant starch in various pH.

FIG. 3d is a graph of Brabender data taken from double mutant (aeaeae/wxwxwx) starch in neutral conditions. Double mutant starches maintain viscosity despite being homozygous for the waxy mutation.

Figure 3E:
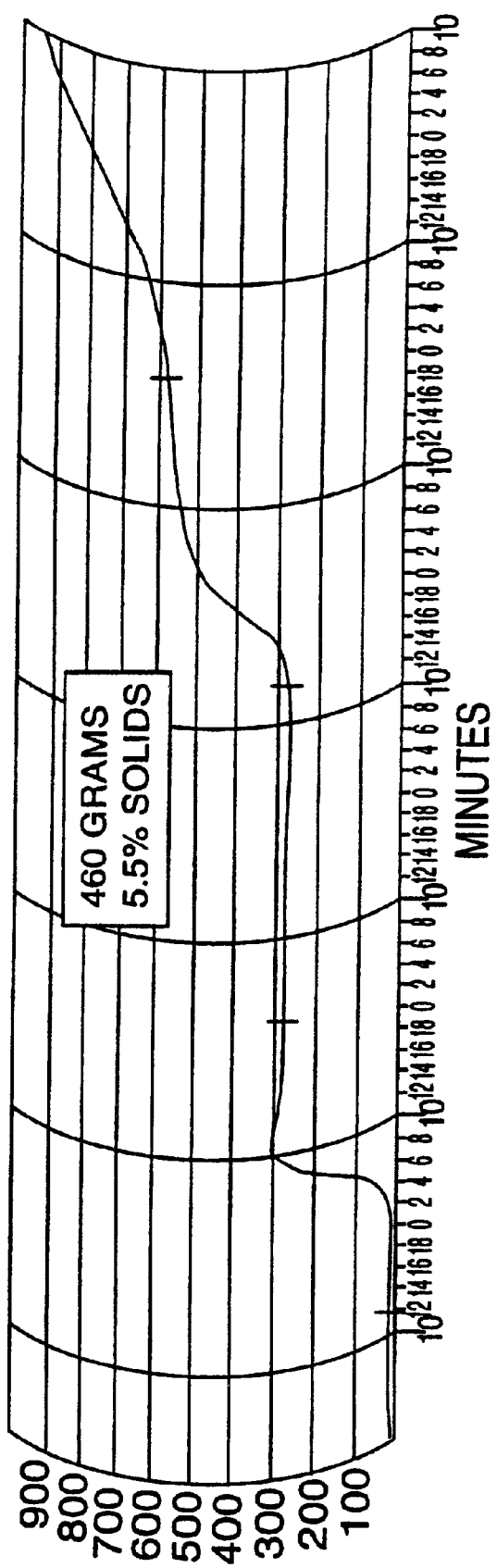
FIG. 3e is a graph of Brabender data of a first intermutant starcg in various pH.

FIG. 3e is a graph of Brabender data taken from intermutant (aeaeAe/WxWxwx) starch in neutral conditions. It is particularly noteworthy from these data that the new intermutant starches provide an increasing strength of viscosity similar to that seen with high amylose mutants, despite containing no increase in apparent amylose content.

Figure 3F:
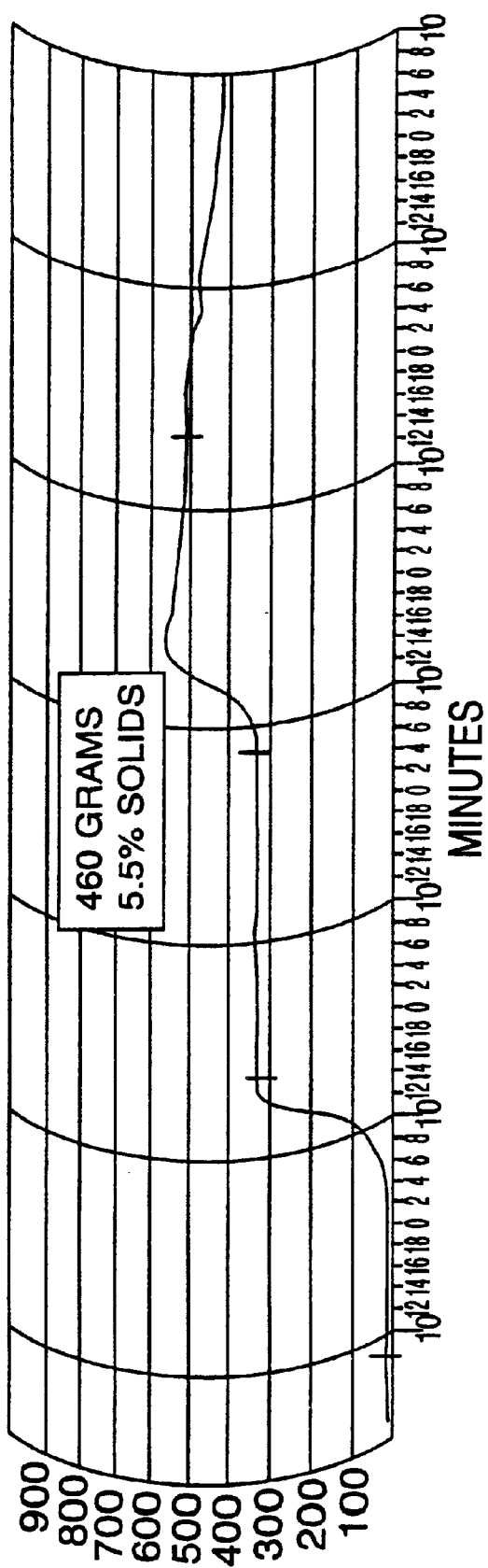
FIG. 3f is a graph of Brabender data of a second intermutant starch in various pH.

FIG. 3f is a graph of Brabender data taken from intermutant (wxwxWx/AeAeae) starch in neutral conditions. It is particularly noteworthy from these data that the new intermutant starches provide an increasing strength of viscosity similar to that seen with high amylose mutants, despite containing no increase in apparent amylose content.

EXAMPLE 2

This example illustrates the production of maize grain possessing starch of the present invention. Maize plants of various backgrounds can be converted to mutant genotypes using either traditional breeding and/or backcrossing techniques or else using mutagenesis such as chemical treatments of pollen. In the alternative, waxy inbreds and hybrids can also be purchased from a number of suppliers and foundation seed companies. Any maize line with good agronomic traits and relatively high yield can be employed. In the present invention, normal inbred lines are converted to mutant inbred lines using chemical mutagenesis followed by careful selection of the mutant grain type from the segregating offspring. This method is well known to those skilled in the art (see for example, Neuffer, M. G. and Chang, M. T. 1989. Induced mutations in biological and agronomic research. Vortr. Pfalzenzuchtg. 16, 165–178). Any commercially valuable inbred line may be used for this process. The lines were confirmed to carry the mutation of interest by an allelism test in which the line may be crossed with a known mutant line, a process well known to those skilled in the art. Furthermore, the kernels from the line will have the appearance and iodine-staining characteristics typical of the mutation selected, a method well known to those skilled in the art. In order to obtain the highest yields from the plants it is best next to produce a hybrid cross between two inbreds, both inbreds carrying the same mutation (e.g., both inbreds being waxy or amylose extender types). It is preferred to produce two hybrids, one being the male and being homozygous for one mutation and the other being the female and being homozygous for the other mutation. The male and female hybrids can be made up of the same or different genetic backgrounds, it is merely important for the two lines to have similar maturities in the field (i.e., require similar heat units from germination to silking and pollen shed). In order to make the intermutant cross in the field it is necessary to eliminate pollen production from the female. This can be done by a variety of methods including, but not limited to, hand pollination, hand and mechanical detasseling, introgressing genetic or cytoplasmic male sterility into the female plants, introducing male sterility through genetic transformation and use of chemical detasseling agents. The grain of this cross contains the present invention with a genotype in the endosperm of aaA/BBb, with the starch from this genotype called intermutant starch. It is well known to those skilled in the art that the genetic background can be optimized for best starch qualities.

EXAMPLE 3

Starch may be extracted from grain by a number of different methods. The most commonly used method involves a "wet milling" procedure known and used throughout the world. The basic principle involves steeping and starch separation. The key step in this process involves softening the grain in a steep tank a process which has been optimized to permit optimal separation of the corn grain components. This method was employed to extract the starch, wxwxWx/AeAeae from the grain of an intermutant developed in accordance with Example 2. The germ was easily liberated intact and freed from adhering endosperm and hull. The endosperm is macerated under water, the starch was easily separated as a white floc and gluten proteins are obtained as a yellow floc. The grain was steeped for 30–40 hrs at 48–52° C. in tanks usually holding 50–90 metric tons of grain. The steep water contains 0.2% sulphur dioxide ($SO_2$ gas is bubbled-in) and so is mildly acidic (pH 4.0). The sulphur dioxide helps break-up the protein matrix permitting the endosperm matrix to break-up into granules. After steeping, the grain were coarsely ground or pulped. The oil-rich embryo floats to the surface and dense starchy endosperm sinks. Separation is achieved through hydroclones (continuous separation). The starch was purified further after being milled through "an impact mill known as Entoleter mill" which smashes the slurry at high speed through counter-rotating grooved plates made of hardened steel alloy, followed by impact with an outer impact ring. The defibered starch was separated from gluten by centrifugation to give two fractions: protein (70% protein) and starch (2% protein). Processing temperature was maintained above 45° C. to prevent microbial growth. The starch was dried by flash-drying by injection into an air stream heated to 200–260° F.

Various intermutant grains can have the starch purified and prepared in this manner is suitable for a variety of food, feed and industrial uses. It may be used directly as unmodified corn starch. It may be modified by chemical or physical treatments that preserve granule structure and granules may be washed to remove residual reactants. Bleaching is sometimes used to create super-white starches. The starch can be gelatinized using a high temperature treatment and sold directly as gelatinized starch. Such starch may be chemically modified and dried. The polymer itself may be hydrolysed partially or completely to produce maltodextrins or glucose. Such products can be further modified by fermentation to produce ethanol for the gasoline industry, or the glucose can be converted to high-fructose corn syrup for the sweetener industry.

EXAMPLE 4

The mutations called shrunken-2 (sh2), brittle-2 (bt2), dull (du), sugary (su), waxy (wx) and amylose extender (ae) encode isoforms of ADP glucose pyrophosphorylase, debranching enzyme, soluble starch synthase, bound starch synthase and branching enzymes:

Shrunken-2 encodes one subunit of ADP glucose pyrophosphorylase,

Brittle-2 encodes one subunit of ADP glucose pyrophosphorylase,

Waxy encodes granule bound starch synthase,

Amylose Extender encodes an isoform of branching enzyme,

Dull alters expression of an isoforms of soluble starch synthase and branching enzyme, Sugary alters expression and activities of soluble starch synthases and debranching enzyme.

Using known mutants and the gene-dosage crossing regimes we have examined the effects of altered gene expression on starch deposition in grain (See figures). With the bt2 mutant we see a progressive loss in measurable ADP Glc pyrophosphorylase activity which correlates well with a loss in starch synthesis in the grain. The control strength exerted by this enzyme over flux to starch cannot be quantified from these data. In fact our studies indicate that this enzyme is one of the major determinants of the duration of starch synthesis and may have little control over rate of starch synthesis. This mutation does not appreciably alter starch structure. When the mutations are with sugary, dull, waxy and amylose extender we now do detect changes in starch fine structure (branched chain length changes as well as changes in amylose/amylopectin ratios). In these cases there is more minor control of flux to starch (except with the sugary mutant which is used to make sweet-corn genotypes). In all of these cases it is the changes in ratios of the starch synthases and branching enzymes which have resulted in alterations in starch fine structure. A dramatic new finding in these studies was the discovery that not only does the mutation reduce expression of key enzymes, but also it induces an overexpression of other enzymes in the pathway. Furthermore, it is only in the full mutant (mmm) genotypes where we see changes in starch fine structure demonstrating that the structural changes occur only when there is an enzyme isoform loss in combination with an enzyme isoform overexpression. Whilst not wishing to be bound by this proposal, these data illustrate the means by which starch structure may be influenced by not only reducing expression (eg using antisense constructs) an enzyme but also be simultaneously increasing expression (eg using sense construct).

Plant transformation vectors for use in the method of the invention may be constructed using standard techniques. Since these enzymes are localized in the amyloplast compartment of the cell, the gene construct requires the presence of an amyloplast transit peptide to ensure its correct localization in the amyloplast. The transformation construct may carry the gene either in the partial sense orientation or in the antisense orientation. Expression of said gene in the plant results in a reduction in expression of the enzyme by effects well known in the art as "sense cosuppression or antisense". When only a reduction in expression is needed the transit peptide is not required. However, when enzyme overexpression is required then a correct plastid targeting sequence is needed in the construct. Key enzymes required for this invention include branching enzyme and soluble and bound starch synthase. Branching enzyme [1,4-α-D-glucan: 1,4-α-D-glucan 6-α-D-(1,4-α-D-glucano ) transferase] converts amylose to amylopectin, (a segment of a 1,4-α-D-glucan chain is transferred to a primary hydroxyl group in a similar glucan chain) sometimes called Q-enzyme. Soluble starch synthase [ADPglucose: 1,4-α-D-glucan 4-α-D-glucosyltransferase] extends the chain-length of amylopectin and perhaps also amylose. Bound starch synthase [ADPglucose:1,4-α-D-glucan 4-α-D-glucosyltransferase] extends the chain length of amylose and perhaps also amylopectin.

For any antisense or sense-cosuppression construct only a partial cDNA clone is required to be expressed in a transgenic plant. Where enzyme overexpression is required, then a full length cDNA clone is needed. The sequence of maize branching enzyme-I was investigated by Baba, T., Nishihara, M., Mizuno, K., Kawasaki, T., Shimada, H., Kobayashi, E., Ohnishi, S., Tanaka, K., and Arai, Y. (Identification, cDNA Cloning, and Gene Expression of Soluble Starch Synthase in Rice (Oryza-sativa L) Immature Seeds. Plant Physiology. 103:565–573, 1993). Starch branching enzyme-II from maize endosperm was investigated by Fisher, D. K., Boyer, C. D., and Hannah, L. C. (Starch Branching Enzyme-II from Maize Endosperm. Plant Physiology. 102:1045–1046, 1993). The article by Mu, C., Harn, C., Ko, Y., Singletary, G. W., Keeling, P. L. and Wasserman, B. P. shows an association of a 76kDa polypeptide with soluble starch synthase 1 activity in maize (cv B73) endosperm. Plant Journal 6, 151–159 (1994). The maize waxy locus for UDP-glucose starch glycosyl transferase was cloned in 1986 by Kloesgen, R. B., Gierl, A., Schwarz-Sommer, Z. and Saedler, H (Molecular analysis of the waxy locus of Zea. Mol. Gen. Genet. 203, 237–244). Recently, the sequence for the maize sugary locus was observed by James, M. and Wright, A. (The Plant Journal) using transposon mutagenesis to locate the gene. The gene for any such protein is thought to be a debranching enzyme and may be used in constructs according to this invention.

It is believed that the chloroplast transit peptides have similar sequences (Heijne et al describe a database of chloroplast transit peptides in 1991, Plant Mol Biol Reporter, 9(2):104–126). Other potential transit peptides are those of ADPG pyrophosphorylase (1991, Plant Mol Biol Reporter, 9:104–126), small subunit RUBISCO, acetolactate synthase, glyceraldehyde-3P-dehydrogenase and nitrite reductase. For example, the consensus sequence of the transit peptide of small subunit RUBISCO from many genotypes has the sequence:

MASSMLSSAAVATRTNPAQASM VAPFTGLKSAAF-PVSRKQNLDITSIAS NGGRVQC

The corn small subunit transit peptide of RUBISCO has the sequence:

MAPTVMMASSATATRTNPAQAS AVAPFQGLK-STASLPVARRSSRSLGN VASNGGRIRC.

The transit peptide of leaf starch synthase from corn has the sequence:

MAALATSQLVATRAGLGVPDAS TFRRGAAQGLR-GARASAAADTL SMRTASARAAPRHQQQAR-RGGR FPSLVVC.

EXAMPLE 5

Figure 4A:
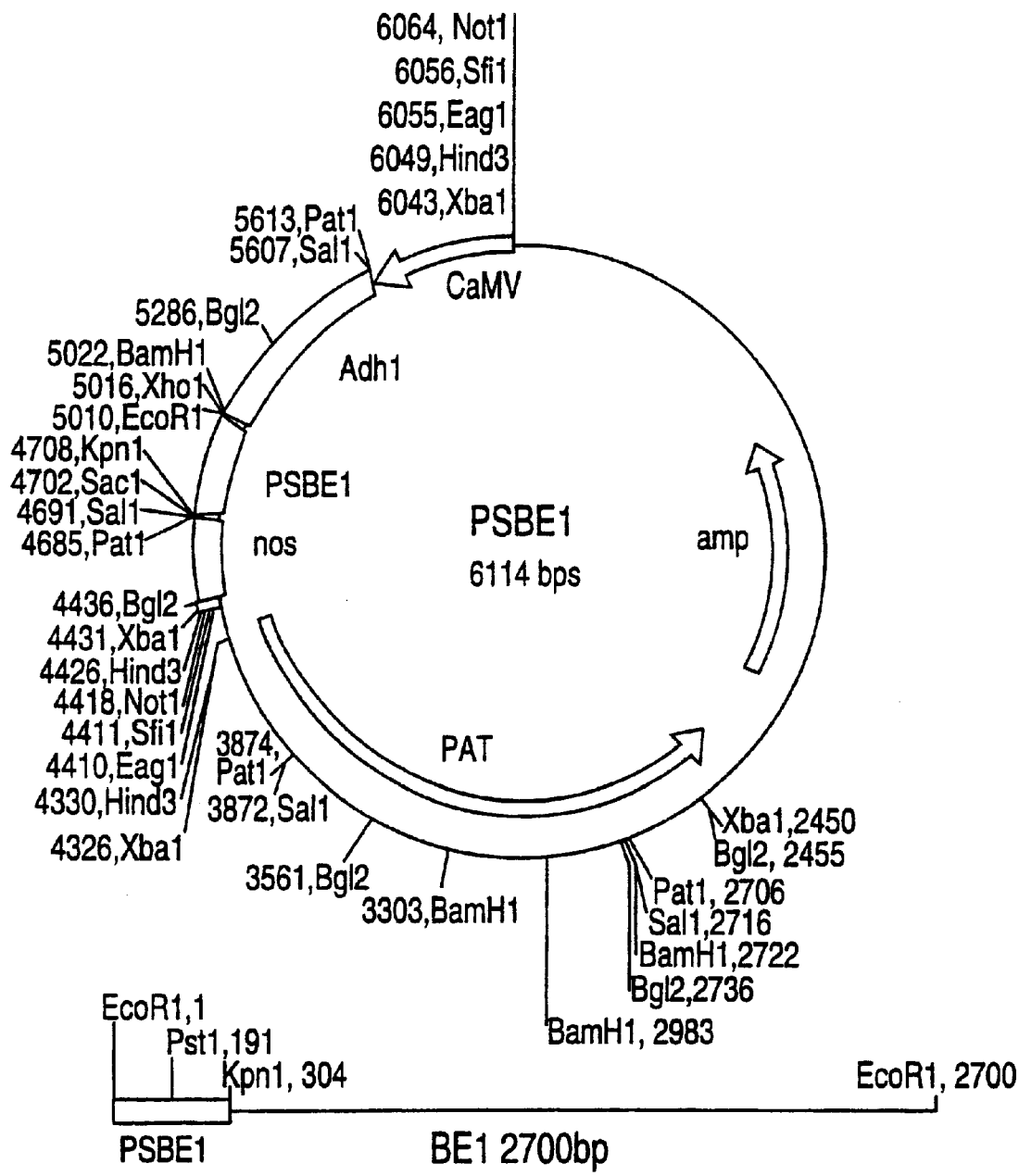
FIG. 4a is a schematic showing the design and restriction enzyme sites of plant transformation vectors used to alter gene expression levels of branching enzyme I.
Figure 4B:
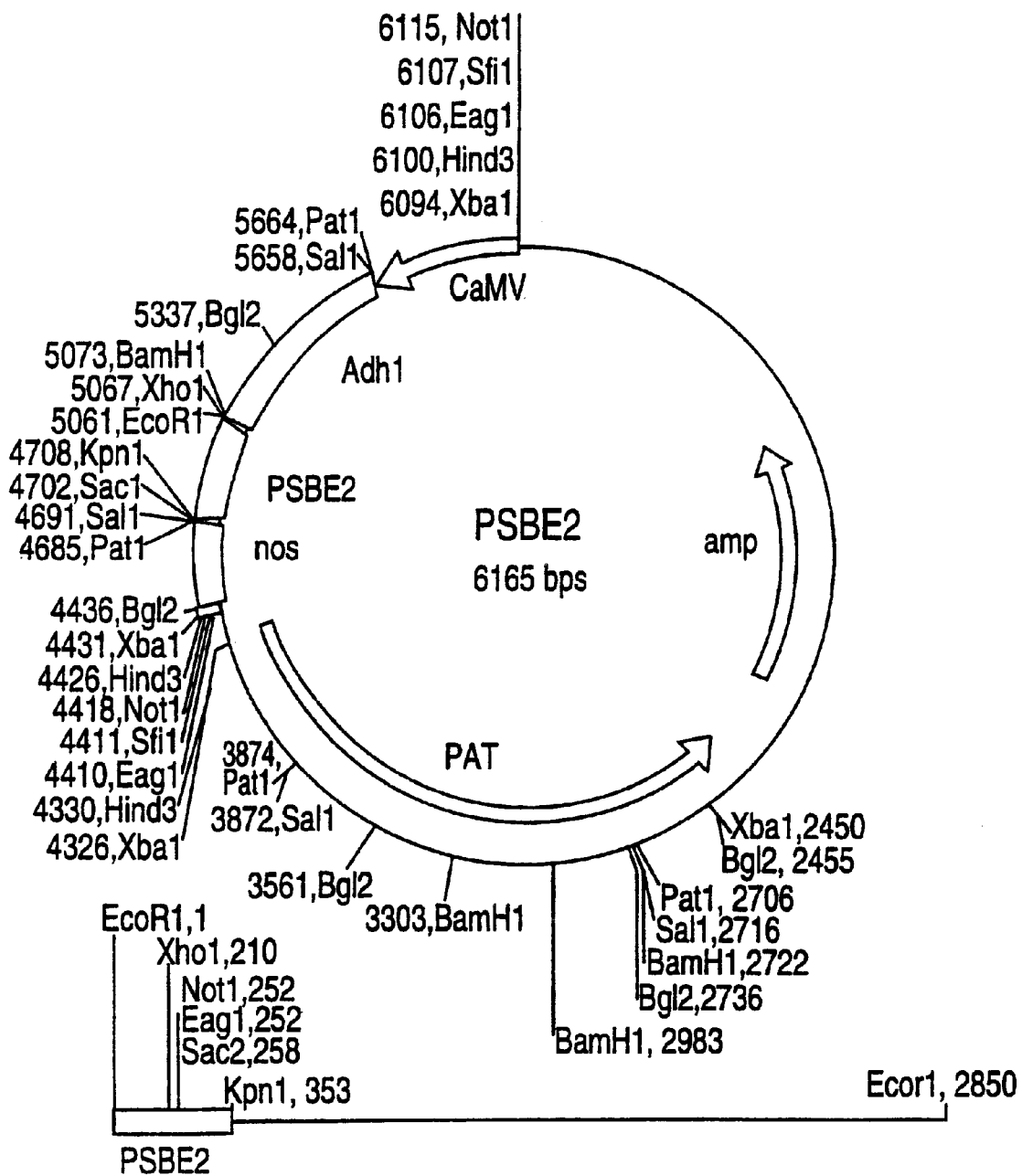
FIG. 4b is a schematic showing the design and restriction enzyme sites of plant transformation vectors used to alter gene expression levels of branching enzyme II.
Figure 4C:
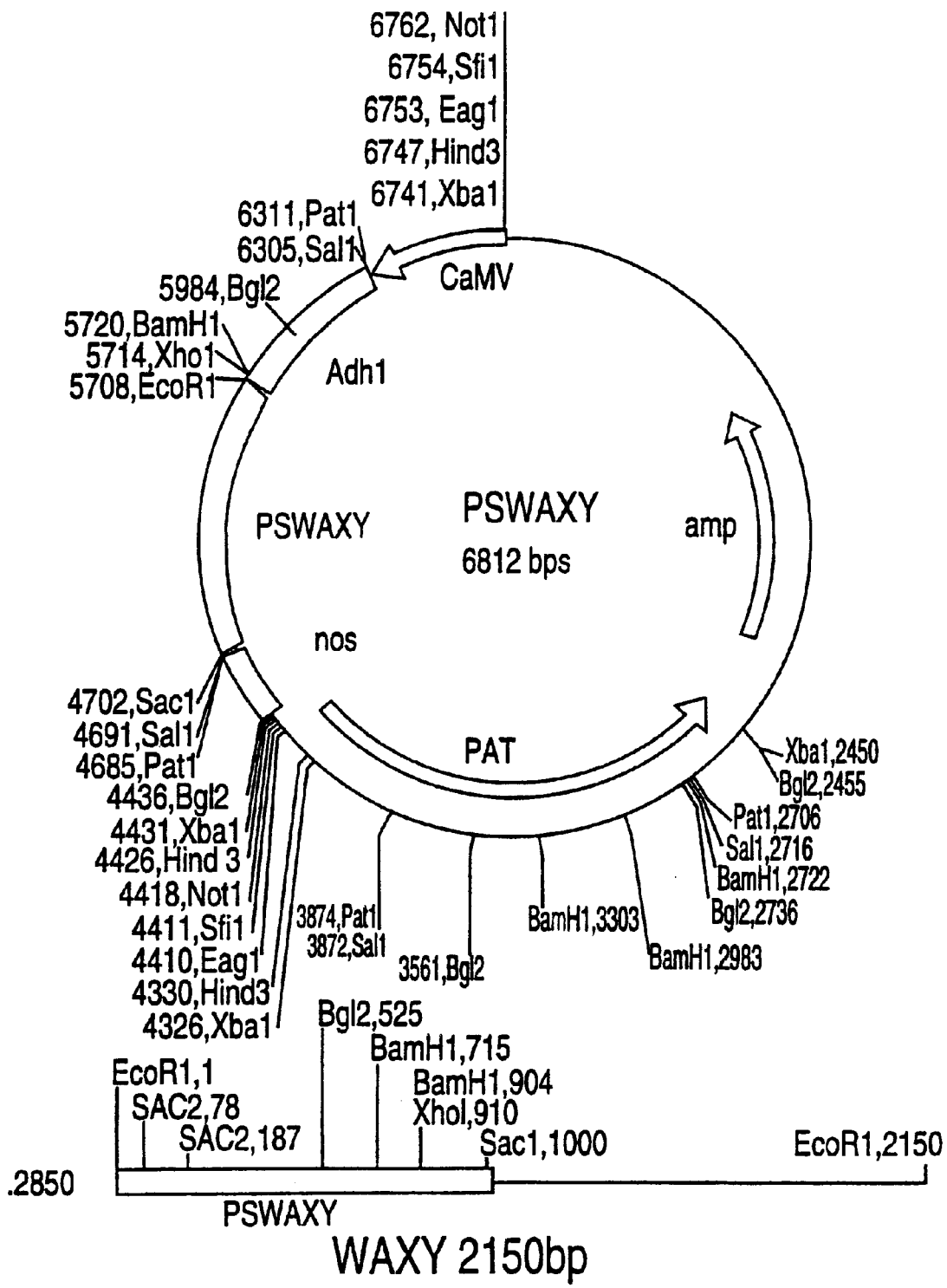
FIG. 4c is a schematic showing the design and restriction enzyme sites of plant transformation vectors used to alter gene expression levels of bound starch synthase (waxy).
Figure 4D:
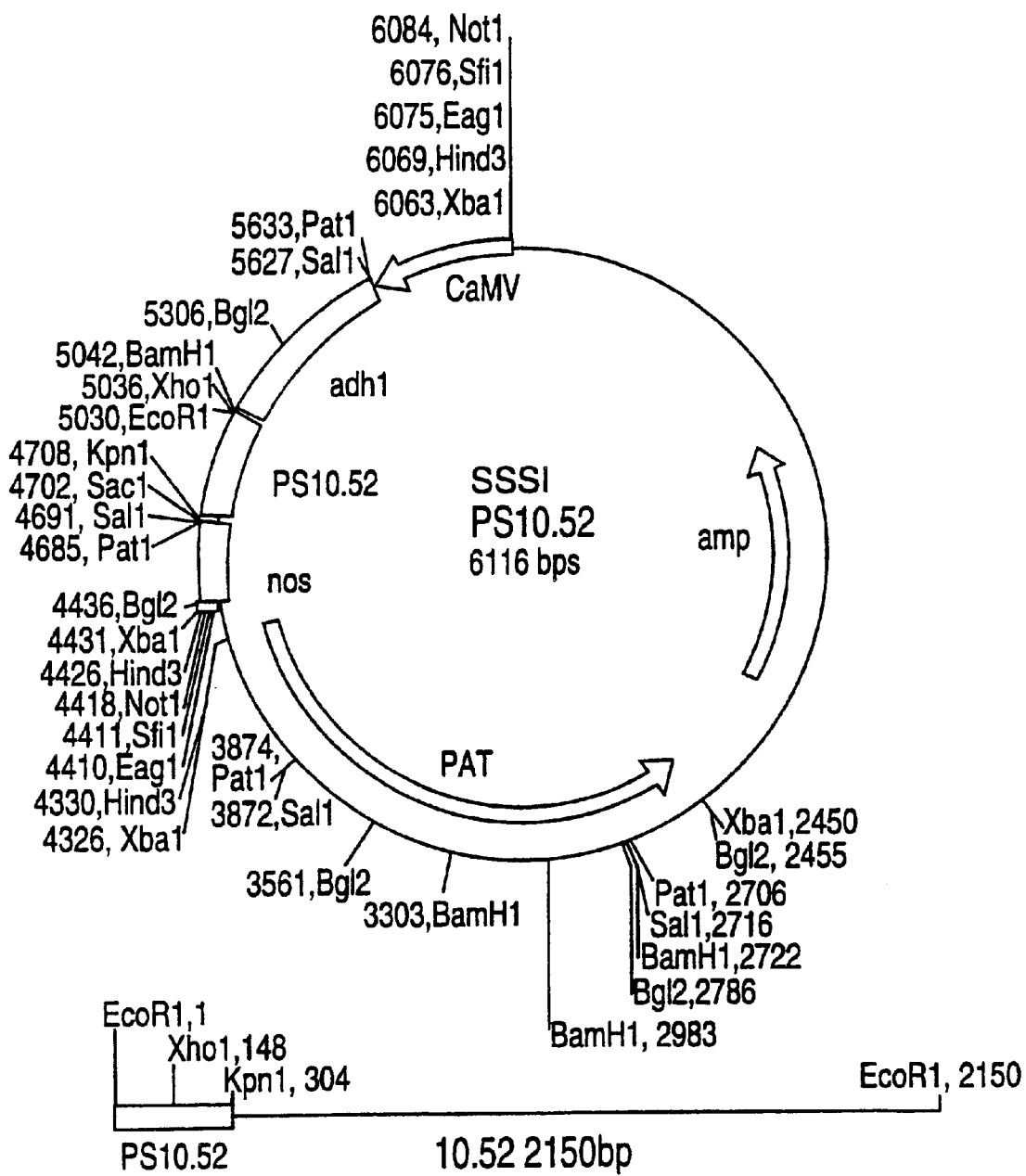
FIG. 4d is a schematic showing the design and restriction enzyme sites of plant transformation vectors used to alter gene expression levels soluble starch synthase.

Production of fertile transgenic maize plants has been done since 1990. Although a number of DNA delivery systems are known, the selection is a particle bombardment. As noted above, constructs of the various maize mutant genes are available from depositories in the U.S. and Europe. Attached are a few examples of some of these constructs as shown in FIGS. 4a–d. FIG. 4c shows a promoter, which is CaMv (cauliflower mosaic virus), an Adhl, the waxy gene, the nos(nopoline), and the pat gene which is useful as a selectable marker and amp. FIG. 4d is similar but shows the soluble starch syntheses first isoform gene in the construct. FIG. 4a again has the same construct but shows the branching enzyme first isoform. FIG. 4b shows the second branching enzyme second isoform. Of course, other constructs associated with the gene mutants used in maize breeding are also available.

For purposes of this example reference is made to FIG. 4c, the waxy construct. The purpose of this experiment is to form an inbred that has partial down regulation of the waxy gene. If the inbred selected is already a mutant for ae, then the grain produced by crossing with a non-mutant inbred will be the grain of an intermutant. Depending on the strength of the down regulation, the female inbreds grain will resemble the mm*/mm* or the mm*/m** type of starch and grain. Clearly, the transformation allows a more precise way of down regulation of the starch synthesis activity such that the alteration of the starch can be finely tuned.

To assure reasonable levels of down regulation of the waxy gene, the transformation target tissue is immature zygotic embryos, through embryogenic callus can also be employed. Immature zygotic embryos from A188 plants 12 days after pollinated with the B73 ae inbred can be selected. The medium for the callus was 6 mM L-proline, 2% (w/v) sucrose, 2 mg/l 2,4-dichlorophenoxyacetic acid (2,4-D) and 0.3% (w/v) Gelrite (Caroline Biological Supply) (pH 6.0). Callus is grown and suspension cultures were initiated.

A MS-based liquid medium containing 100 mg/l myo-inositol, 2 mg/l 2,4-D, 2 mg/l 1-naphthalenacetic acid (NAA), 6 mM proline, 200 mg/l casein hydrolysate (Difco Laboratories), 3% (w/v) sucrose, and 5% (v/v) coconut water (Difco Laboratories) (pH 6.0). Cell suspensions were maintained in this medium in 125 ml Erlenmeyer flasks at 28° C. in the dark on a gyrating shaker at 125 rpm.

The transformation vector in FIG. 4c is selected. This plasmid contains a 355-1 adh-pat nos 3' selectable gene expression cassette.

The cell suspensions are sieved and then suspended in 5 ml of suspension medium and placed on filter paper through vacuum. The construct was coated into particles as is know in the art. The plates were then bombarded. The cells are then transferred to a N-6 medium and after 14 days transformed cells are selected by 1 mg/l bialaphos. The cells are then suspended in a medium containing 0.6% (w/v) (Sea-Plaque; FMC) and held at 37° C.

Two to five weeks later, growing calli are removed and transferred to the surface of fresh selection medium. Plants were regenerated in a MS based medium having 6% sucrose 1 g/l myo-inositol, 1 mg/l NAA (34), and 0.3% (w/v) Gelrite (pH 6.0). Next the embryo germination occurred in a MS media of 0.25 mg/l NAA and 3% (w/v) sucrose and light. Plants are grown and transferred to the greenhouse. The expression levels in the plant can then be evaluated.

The plant is bred and developed to an inbred having the mutant and the down regulated pathway. Alternatively, the selected inbred can have the mutant crossed onto a transgenic after transformation to form the desired starch in the grain when the transgenic plant is employed as the female.

Accordingly, the present invention has been described with some degree of particularity directed to the preferred embodiment of the present invention. It should be appreciated, though, that the present invention is defined by the following claims construed in light of the prior art so that modifications or changes may be made to the preferred embodiment of the present invention without departing from the inventive concepts contained herein.

We claim:

1. A starch gel comprising starch extracted from a plant grain having a wild-type triploid endosperm genotype composed of 1 or 2 doses of a recessive mutant allele of a first gene and 1 or 2 doses of a recessive mutant allele of a second gene wherein said first and second genes are independently selected from the group of genes consisting of waxy, amylose extender, dull, horny, sugary, shrunken, brittle, floury and opaque, such that when said first gene and said second gene are not waxy, said wild-type triploid endosperm genotype is not homozygous recessive at the waxy gene.

2. A starch gel comprising starch extracted from a plant grain having a wild-type triploid endosperm genotype composed of 1 or 2 doses of a recessive mutant allele of a first gene and 1 or 2 doses of a recessive mutant allele of a second gene and 1 or 2 doses of a recessive mutant allele of a third gene wherein said first and second and third genes are independently selected from the group of genes consisting of waxy, amylose extender, dull, horny, sugary, slinking, brittle, floury and opaque; such that when said first gene, said second gene and said third gene are not waxy, said wild-type triploid endosperm genotype is not homozygous recessive at the waxy gene.

3. The starch gel of claim 1 wherein said first gene or said second gene is waxy.

4. The starch gel of claim 2 wherein said first gene or said second gene is waxy.

5. The starch gel of claim 1 wherein said first gene or said second gene is amylose extender.

6. The starch gel of claim 2 wherein said first gene or said second gene is amylose extender.

7. The starch gel of claim 1 wherein said first gene or said second gene is dull.

8. The starch gel of claim 2 wherein said first gene or said second gene is dull.

9. The starch gel of claim 1 wherein said first gene or said second gene is horny.

10. The starch gel of claim 2 wherein said first gene or said second gene is horny.

11. The starch gel of claim 1 wherein said first gene or said second gene is sugary.

12. The starch gel of claim 2 wherein said first gene or said second gene is sugary.

13. The starch gel of claim 2 wherein said first gene or said second gene is shrunken.

14. The starch gel of claim 2 wherein said first gene or said second gene is shrunken.

15. The starch gel of claim 1 wherein said first gene or said second gene is brittle.

16. The starch gel of claim 1 wherein said first gene or said second gene is brittle.

17. The starch gel of claim 1 wherein said first gene or said second gene is floury.

18. The starch gel of claim 2 wherein said first gene or said second gene is floury.

19. The starch gel of claim 1 wherein said first gene or said second gene is opaque.

20. The starch gel of claim 2 wherein said first gene or said second gene is opaque.

21. The starch gel of claim 1 wherein said plant is a corn plant.

22. The starch gel of claim 2 wherein said plant is a corn plant.

23. A starch gel according to claim 1, wherein said first and second genes are independently selected from the group consisting of amylose extender, dull, horny, sugary, brittle, floury and opaque.

24. A starch gel according to claim 2, wherein said first, second and third genes are independently selected from the group consisting of amylose extender, dull, horny, sugary, brittle, floury and opaque.

25. A starch gel according to claim 1, wherein said first and second genes are independently selected from the group consisting of waxy, dull, horny, sugary, shrunken, brittle, floury and opaque.

26. A starch gel according to claim 2, wherein said first, second and third genes are independently selected from the group consisting of waxy, dull, horny, sugary, shrunken, brittle, floury and opaque.

27. A starch gel according to claim 1, wherein said genotype is composed of 2 doses of said first gene and 2 doses of said second gene.

28. A starch gel according to claim 2, wherein said genotype is composed of 2 doses of said first gene and 2 doses of said second gene.

29. A starch gel according to claim 23, wherein said genotype is composed of 2 doses of said first gene and 2 doses of said second gene.

30. A starch gel according to claim 24, wherein said genotype is composed of 2 doses of said first gene and 2 doses of said second gene.

31. A starch gel according to claim 25, wherein said genotype is composed of 2 doses of said first gene and 2 doses of said second gene.

32. A starch gel according to claim 26, wherein said genotype is composed of 2 doses of said first gene and 2 doses of said second gene.

33. A starch gel according to claim 1, wherein said genotype is composed of 1 dose of said first gene and 2 doses of said second gene.

34. A starch gel according to claim 2, wherein said genotype is composed of 1 dose of said first gene and 2 doses of said second gene.

35. A starch gel according to claim 23, wherein said genotype is composed of 1 dose of said first gene and 2 doses of said second gene.

36. A starch gel according to claim 24, wherein said genotype is composed of 1 dose of said first gene and 2 doses of said second gene.

37. A starch gel according to claim 25, wherein said genotype is composed of 1 dose of said first gene and 2 doses of said second gene.

38. A starch gel according to claim 26, wherein said genotype is composed of 1 dose of said first gene and 2 doses of said second gene.

* * * * *